(12) United States Patent
Thamhesl et al.

(10) Patent No.: US 12,371,681 B2
(45) Date of Patent: Jul. 29, 2025

(54) MEANS AND METHODS FOR CLEAVAGE OF ZEARALENONE

(71) Applicant: DSM Austria GmbH, Getzersdorf (AT)

(72) Inventors: Michaela Thamhesl, Goellersdorf (AT); Sebastian Fruhauf, Tulln (AT); Wulf-Dieter Moll, Stockerau (AT); Andreas Hoebartner, Obermeisling (AT); Gerd Schatzmayr, Tulln (AT); Eva Maria Binder, Tulln (AT); Markus Aleschko, Vienna (AT); Martin Pfeffer, Tulln (AT)

(73) Assignee: DSM Austria GmbH, Getzersdorf (AT)

( * ) Notice: Subject to any disclaimer, the term of this patent is extended or adjusted under 35 U.S.C. 154(b) by 1143 days.

(21) Appl. No.: 17/264,096

(22) PCT Filed: Jul. 30, 2019

(86) PCT No.: PCT/EP2019/070434
§ 371 (c)(1),
(2) Date: Jan. 28, 2021

(87) PCT Pub. No.: WO2020/025580
PCT Pub. Date: Feb. 6, 2020

(65) Prior Publication Data
US 2021/0371835 A1   Dec. 2, 2021

(30) Foreign Application Priority Data
Jul. 31, 2018  (EP) ..................................... 18186532

(51) Int. Cl.
*C12N 9/14* (2006.01)
*A23K 20/189* (2016.01)
(Continued)

(52) U.S. Cl.
CPC .............. *C12N 9/14* (2013.01); *A23K 20/189* (2016.05); *A23K 50/30* (2016.05); *A23K 50/60* (2016.05);
(Continued)

(58) Field of Classification Search
CPC ................................. C12N 9/14; A61K 38/46
See application file for complete search history.

(56) References Cited

U.S. PATENT DOCUMENTS 6,794,175 B1    9/2004  Binder et al.
10,149,489 B2  12/2018  Fruhauf et al.
(Continued)

FOREIGN PATENT DOCUMENTS

CN    108085306 A     5/2018
WO     99/35240 A1     7/1999
WO  2012/113827 A1     8/2012

OTHER PUBLICATIONS

UNIPROT Database accession No. A0A1V4A9G7; Alpha/beta hydrolase-1 amino acid sequence, Jun. 7, 2017, 1 page.
(Continued)

*Primary Examiner* — David W Berke-Schlessel
*Assistant Examiner* — Trent R Clarke
(74) *Attorney, Agent, or Firm* — Mueting Raasch Group

(57) ABSTRACT

The present invention relates to a method for increasing the stability of an α/β-hydrolase. In addition, the present invention relates to an α/β-hydrolase obtainable by the method of the present invention. Also provided are α/β-hydrolases having a decreased grand average of hydropathy (GRAVY) value and/or comprising specific mutations. In addition, the present invention concerns a use of an α/β-hydrolase of the present invention for degrading zearalenone (ZEN).

11 Claims, 11 Drawing Sheets
Specification includes a Sequence Listing.

| | | |
|---|---|---|
| V160A | -0.174 | 4.2 |
| G185R | -0.180 | 7.8 |
| G185S | -0.168 | 0.6 |
| A186P | -0.178 | 6.6 |
| A186R | -0.187 | 12.0 |
| A186D | -0.184 | 10.2 |
| A188H | -0.183 | 9.6 |
| A188N | -0.184 | 10.2 |
| A188G | -0.174 | 4.2 |
| A188R | -0.187 | 12.0 |
| S189D | -0.175 | 4.8 |
| P190H | -0.172 | 3.0 |
| M191D | -0.184 | 10.2 |
| G199E | -0.177 | 6.0 |
| I200A | -0.175 | 4.8 |
| I200V | -0.168 | 0.6 |
| H203N | -0.168 | 0.6 |
| Q205K | -0.168 | 0.6 |
| G185R/A188N | -0.197 | 16.9 |
| G185S/A188R | -0.188 | 12.6 |
| G185R/A186R/A188H/S189D/P190H/M191D | -0.218 | 30.5 |
| V160A/G185R/A188N/G199E/I200A/H203N/Q205K | -0.226 | 35.2 |
| V160A/G185S/A188R/G199E/I200A/H203N/Q205K | -0.217 | 29.9 |
| V160A/G199E/I200A/H203N/Q205K | -0.195 | 17.7 |
| V160A/G185R/A186R/A188H/G199E/I200V/H203N/Q205K | -0.238 | 42.5 |

(51) Int. Cl.
  *A23K 50/30*   (2016.01)
  *A23K 50/60*   (2016.01)
  *A23K 50/75*   (2016.01)
  *A23L 29/00*   (2016.01)
  *A23L 33/00*   (2016.01)
  *A23L 33/10*   (2016.01)
  *A61K 38/46*   (2006.01)

(52) U.S. Cl.
  CPC .............. *A23K 50/75* (2016.05); *A23L 29/06* (2016.08); *A23L 33/10* (2016.08); *A23L 33/40* (2016.08); *A61K 38/46* (2013.01); *A23V 2002/00* (2013.01)

(56) References Cited

U.S. PATENT DOCUMENTS

| | | | |
|---|---|---|---|
| 2016/0319258 | A1 | 11/2016 | Fruhauf et al. |
| 2016/0345606 | A1* | 12/2016 | Fruhauf .................. C12N 9/18 |
| 2019/0124948 | A1 | 5/2019 | Fruhauf et al. |

OTHER PUBLICATIONS

Geneseq Database accession No. BBV29130 R. erythropolis Hydrolase mutant (Q296E/H298V/L302S/L307Q/F308S) amino acid sequence, Apr. 23, 2015.
Xiang, La et al., (2016) "High-level expression of a ZEN-detoxifying gene by codon optimization and biobrick in Pichia pastoris", Microbiological Research, 193:48-56.
NCBI Protein Accession No. WP_108990044: alpha/beta hydrolase [Streptomyces coelicoflavus] (309 aa), Apr. 1, 2023, 1 page.
NCBI Protein Accession No. WP_007388500: Multispecies: alpha/beta hydrolase [Streptomyces] (309 aa), Apr. 1, 2023, 1 page.
Altschul, S.F., "A Protein Alignment Scoring System Sensitive at All Evolutionary Distances," Journal of Molecular Evolution, vol. 36, No. 3, Mar. 1993, pp. 290-300.
Altschul et al., "Basic Local Alignment Search Tool," Journal of Molecular Biology, vol. 215, No. 3, Oct. 1990, pp. 403-410.
Altschul et al., "Gapped BLAST and PSI-BLAST: a new generation of protein database search programs," Nucleic Acids Research vol. 25, No. 17, Sep. 1997, pp. 3389-3402.
Biehl et al., "Biliary Excretion and Enterohepatic Cycling of Zearalenone in Immature Pigs," Toxicology and Applied Pharmacology, vol. 121, No. 1, Jul. 1993, pp. 152-159.
Brutlag et al., "Improved sensitivity of biological sequence database searches," Bioinformatics, vol. 6, No. 3, Jul. 1990, pp. 237-245.
Burnley et al., "phenix.ensemble_refinement: a test study of apo and holo BACE1," Computational Crystallography Newsletters, vol. 4, 2013, pp. 51-58.
Carr et al., "α/βHydrolase Fold: An Update," Protein & Peptide Letters, vol. 16, No. 10, 2009, pp. 1137-1148. (Abstract Only).
Cregg, J.M., "Chapter 1—Introduction—Distinctions Between Pichia pastoris and Other Expression Systems," from Methods in Molecular Biology, vol. 389: Pichia Protocols, Second Edition, Edited by: J.M. Cregg, © Humana Press Inc., Totowa, NJ, 2007, pp. 1-259. (Filed in 2 parts).
Creighton, T.E., "Section 2.4.3 Glycosylation from Chapter 2 Biosynthesis of Proteins, Section 2.4 Posttranslational Covalent Modifications of Polypeptide Chains" from Proteins Structures and Molecular Properties, Second Edition, W.H. Freeman and Company, New York, 1993, pp. 91-93. (includes title and copyright pages).

Gasteiger et al., "Chapter 52—Protein Identification and Analysis Tools on the ExPASy Server," from The Proteomics Protocols Handbook, Edited by J.M. Walker @ Humana Press Inc., Totowa, N.J., 2005, pp. 571-607.
International Search Report and Written Opinion of International Application No. PCT/EP2019/070434, dated Sep. 20, 2019, 12 pp.
Jantratid et al., "Dissolution Media Simulating Conditions in the Proximal Human Gastrointestinal Tract: An Update," Pharmaceutical Research, vol. 25, No. 7, Apr. 2008, pp. 1663-1676.
Jones, D.T., "Protein Secondary Structure Prediction Based on Position-specific Scoring Matrices," Journal of Molecular Biology, vol. 292, No. 2, Sep. 1999, pp. 195-202.
Kourist et al., "The α/β-Hydrolase Fold 3DM Database (ABHDB) as a Tool for Protein Engineering," ChemBioChem, vol. 11, No. 12, Aug. 2010, pp. 1635-1643.
Krieger et al., "YASARA View-molecular graphics for all devices-from smartphones to workstations," Bioinformatics, vol. 30, No. 20, Jul. 2014, pp. 2981-2982.
Kurtzman, C.P., "Biotechnological strains of Komagataella (Pichia) pastoris are Komagataella phaffii as determined from multigene sequence analysis," Journal of Industrial Microbiology & Biotechnology, vol. 36, No. 11, Nov. 2009, pp. 1435-1438.
Kyte et al., "A Simple Method for Displaying the Hydropathic Character of a Protein," Journal of Molecular Biology, vol. 157,No. 1, May 1982, pp. 105-132.
Lenfant et al., "ESTHER, the database of the α/β-hydrolase fold superfamily of proteins: tools to explore diversity of functions," Nucleic Acid Research, vol. 41 (Database Issue), Nov. 2012, pp. D423-D429.
Malekinejad et al., "Hydroxysteroid Dehydrogenases in Bovine and Porcine Granulosa Cells Convert Zearalenone into its Hydroxylated Metabolites α-Zearalenol and β-Zearalenol," Veterinary Research Communications, vol. 30, No. 4, May 2006, pp. 445-453.
Mindrebo et al., "Unveiling the functional diversity of the alpha/beta hydrolase superfamily in the plant kingdom," Current Opinion in Structural Biology, vol. 41, Sep. 2016, pp. 233-246 and Corrigendum consisting of 3 pages.
Ollis et al., "The α/β hydrolase fold," Protein Engineering, Design and Selection, vol. 5, No. 3, Apr. 1992, pp. 197-211.
Rattan et al., "Protein Synthesis, Posttranslational Modification, and Aging," Annals of the New York Academy of Sciences, vol. 663, Nov. 1992, pp. 48-62.
Schatzmayr et al., "Global occurrence of mycotoxins in the food and feed chain: facts and figures," World Mycotoxin Journal, vol. 6, No. 3, Jul. 2013, pp. 213-222.
Seifter et al., "Chapter 47—Analysis for Protein Modifications and Nonprotein Cofactors," in Methods in Enzymology, vol. 182, 1990, pp. 626-646.
Stenhagen et al., "Electrophoretic Behaviour in Nucleic Acid-Protein Mixtures," Nature, vol. 141, Mar. 1938, pp. 415.
Thompson et al., "Clustal W: improving the sensitivity of progressive multiple sequence alignment through sequence weighting, position-specific gap penalties and weight matrix choice," Nucleic Acids Research, vol. 22, No. 22, Nov. 1994, pp. 4673-4680.
Vekiru et al., "Isolation and characterization of enzymatic zearalenone hydrolysis reaction products," World Mycotoxin Journal, vol. 9, No. 3, Apr. 2016, pp. 353-363.
Wold, F., "Posttranslational Protein Modifications: Perspectives and Prospectives," in Posttranslational Covalent Modifications of Proteins, Edited by B. Connor Johnson, Academic Press, 1983, in particular to pp. 1-12. (submitting) 423 pages).
Yamada et al., "The Phylogenetic Relationships of Methanol-assimilating Yeasts Based on the Partial Sequences of 18S and 26S Ribosomal RNAs: The Proposal of Komagataella Gen. Nov. (*Saccharomycesaceae*)," Bioscience, Biotechnology, and Biochemistry, vol. 59, No. 3, Jan. 1995, pp. 439-444.

\* cited by examiner

FIGURE 1

| ZEN-degrading α/β-hydrolase | CAP-domain (positions from first to last amino acid) | VI-domain (positions from first to last amino acid) | CAP-loop (positions from first to last amino acid) |
|---|---|---|---|
| SEQ ID NO: 1 | 145-218 | 160-205 | 185-191 |
| SEQ ID NO: 2 | 144-217 | 159-204 | 184-190 |
| SEQ ID NO: 3 | 145-218 | 160-205 | 185-191 |
| SEQ ID NO: 4 | 145-218 | 160-205 | 185-191 |
| SEQ ID NO: 5 | 145-218 | 160-205 | 185-191 |
| SEQ ID NO: 6 | 161-235 | 176-222 | 201-208 |

FIGURE 2A:

| Modification(s) of SEQ ID NO: 1 present in the VI-domain | GRAVY values of SEQ ID NO: 1 variants | Decrease of GRAVY values of variants relative to SEQ ID NO: 1 (%) |
|---|---|---|
| V160A | -0.174 | 4.2 |
| G185R | -0.180 | 7.8 |
| G185S | -0.168 | 0.6 |
| A186P | -0.178 | 6.6 |
| A186R | -0.187 | 12.0 |
| A188D | -0.184 | 10.2 |
| A188H | -0.183 | 9.6 |
| A188N | -0.184 | 10.2 |
| A188G | -0.174 | 4.2 |
| A188R | -0.187 | 12.0 |
| S189D | -0.175 | 4.8 |
| P190H | -0.172 | 3.0 |
| M191D | -0.184 | 10.2 |
| G199E | -0.177 | 6.0 |
| I200A | -0.175 | 4.8 |
| I200V | -0.168 | 0.6 |
| H203N | -0.168 | 0.6 |
| Q205K | -0.168 | 0.6 |
| | | |
| G185R/A188N | -0.197 | 18.0 |
| G185S/A188R | -0.188 | 12.6 |
| G185R/A186R/A188H/S189D/P190H/M191D | -0.218 | 30.5 |
| V160A/G185R/A188N/G199E/I200A/H203N/Q205K | -0.226 | 35.2 |
| V160A/G185S/A188R/G199E/I200A/H203N/Q205K | -0.217 | 29.9 |
| V160A/G199E/I200A/H203N/Q205K | -0.195 | 17.7 |
| V160A/G185R/A186R/A188H/G199E/I200V/H203N/Q205K | -0.238 | 42.5 |

FIGURE 2B:

| Modification(s) of SEQ ID NO: 1 present in the VI-domain | GRAVY value of CAP-domain of SEQ ID NO: 1 variants | Decrease of GRAVY values of CAP-domain of variants relative to CAP-domain of SEQ ID NO: 1 (%) |
|---|---|---|
| V160A | -0.316 | 11.3 |
| G185R | -0.339 | 19.4 |
| G185S | -0.289 | 1.8 |
| A186P | -0.330 | 16.2 |
| A186R | -0.369 | 29.9 |
| A188D | -0.355 | 25.0 |
| A188H | -0.351 | 23.6 |
| A188N | -0.355 | 25.0 |
| A188G | -0.314 | 10.6 |
| A188R | -0.369 | 29.9 |
| S189D | -0.320 | 12.7 |
| P190H | -0.305 | 7.4 |
| M191D | -0.357 | 25.7 |
| G199E | -0.326 | 14.8 |
| I200A | -0.320 | 12.7 |
| I200V | -0.288 | 1.4 |
| H203N | -0.288 | 1.4 |
| Q205K | -0.289 | 1.8 |
| G185R/A188N | -0.411 | 44.7 |
| G185S/A188R | -0.374 | 31.7 |
| G185R/A186R/A188H/S189D/P190H/M191D | -0.500 | 76.1 |
| V160A/G185R/A188N/G199E/I200A/H203N/Q205K | -0.531 | 87.0 |
| V160A/G185S/A188R/G199E/I200A/H203N/Q205K | -0.495 | 74.3 |
| V160A/G199E/I200A/H203N/Q205K | -0.404 | 42.3 |
| V160A/G185R/A186R/A188H/G199E/I200V/H203N/Q205K | -0.580 | 104.2 |

FIGURE 2C:

| Modification(s) of SEQ ID NO: 1 present in the VI-domain | GRAVY value of VI-domain of SEQ ID NO: 1 variants | Decrease of GRAVY values of VI-domain of variants relative to VI-domain of SEQ ID NO: 1 (%) |
|---|---|---|
| V160A | -0.096 | 123.3 |
| G185R | -0.133 | 209.3 |
| G185S | -0.052 | 20.9 |
| A186P | -0.117 | 172.1 |
| A186R | -0.180 | 318.6 |
| A188D | -0.159 | 269.8 |
| A188H | -0.152 | 253.5 |
| A188N | -0.159 | 269.8 |
| A188G | -0.091 | 111.6 |
| A188R | -0.180 | 318.6 |
| S189D | -0.102 | 137.2 |
| P190H | -0.078 | 81.4 |
| M191D | -0.161 | 274.4 |
| G199E | -0.111 | 158.1 |
| I200A | -0.102 | 137.2 |
| I200V | -0.050 | 16.3 |
| H203N | -0.050 | 16.3 |
| Q205K | -0.052 | 20.9 |
| G185R/A188N | -0.248 | 476.7 |
| G185S/A188R | -0.189 | 339.5 |
| G185R/A186R/A188H/S189D/P190H/M191D | -0.391 | 809.3 |
| V160A/G185R/A188N/G199E/I200A/H203N/Q205K | -0.441 | 925.6 |
| V160A/G185S/A188R/G199E/I200A/H203N/Q205K | -0.383 | 790.7 |
| V160A/G199E/I200A/H203N/Q205K | -0.237 | 451.2 |
| V160A/G185R/A186R/A188H/G199E/I200V/H203N/Q205K | -0.520 | 1109

FIGURE 2D:

| Modification(s) of SEQ ID NO:1 present in the CAP-loop | GRAVY values of CAP-loop of SEQ ID NO: 1 variants | Decrease of GRAVY values of CAP-loop of variants relative to CAP-loop of SEQ ID NO: 1 (%) |
|---|---|---|
| G185R | -0.314 | 215.9 |
| G185S | 0.214 | 21.0 |
| A186P | -0.214 | 179.0 |
| A186R | -0.629 | 332.1 |
| A188D | -0.486 | 279.3 |
| A188H | -0.443 | 263.5 |
| A188N | -0.486 | 279.3 |
| A188G | -0.043 | 115.9 |
| A188R | -0.629 | 332.1 |
| S189D | -0.144 | 153.2 |
| P190H | 0.043 | 84.1 |
| M191D | -0.500 | 284.5 |
| G185R/A188N | -1.071 | 495.2 |
| G185S/A188R | -0.686 | 353.2 |
| G185R/A186R/A188H | -1.929 | 811.8 |
| G185R/A186R/A188H/S189D/P190H/M191D | -3.314 | 1322.9 |

FIGURE 2E:

| Modification(s) of SEQ ID NO: 6 present in the VI-domain | GRAVY values of SEQ ID NO: 6 variants | Decrease of GRAVY values of variants relative to SEQ ID NO: 6 (%) |
|---|---|---|
| F183Y | -0.204 | 6.3 |
| V197C | -0.197 | 2.6 |
| F183Y/V197C | -0.209 | 8.9 |

FIGURE 2F:

| Modification(s) of SEQ ID NO: 6 present in the VI-domain | GRAVY values of CAP-domain of SEQ ID NO: 6 variant | Decrease of GRAVY values of CAP-domain of variants relative to CAP-domain of SEQ ID NO: 6 (%) |
|---|---|---|
| F183Y | -0.443 | 14.2 |
| V197C | -0.411 | 5.9 |
| F183Y/V197C | -0.465 | 19.9 |

Figure 2G:

| Modification(s) of SEQ ID NO: 6 present in the VI-domain | GRAVY values of VI-domain of SEQ ID NO: 6 variant | Decrease of GRAVY values of VI-domain of variants relative to VI-domain of SEQ ID NO: 6 (%) |
|---|---|---|
| F183Y | -0.555 | 18.6 |
| V197C | -0.504 | 7.7 |
| F183Y/V197C | -0.591 | 26.3 |

FIGURE 3A:

| Modification(s) of SEQ ID NO: 1 | Increase in T(50%) (%) | Region |
|---|---|---|
| V160A | 3.4 | CAP-domain - VI-domain |
| G185R | 3.4 | CAP-domain - VI-domain - CAP-loop |
| G185S | 2.2 | CAP-domain - VI-domain - CAP-loop |
| A186P | 3.4 | CAP-domain - VI-domain - CAP-loop |
| A186R | 4.3 | CAP-domain - VI-domain - CAP-loop |
| A188D | 3.4 | CAP-domain - VI-domain - CAP-loop |
| A188H | 3.4 | CAP-domain - VI-domain - CAP-loop |
| A188N | 2.2 | CAP-domain - VI-domain - CAP-loop |
| A188G | 3.4 | CAP-domain - VI-domain - CAP-loop |
| A188R | 5.8 | CAP-domain - VI-domain - CAP-loop |
| S189D | 3.4 | CAP-domain - VI-domain - CAP-loop |
| P190H | 4.3 | CAP-domain - VI-domain - CAP-loop |
| M191D | 2.2 | CAP-domain - VI-domain - CAP-loop |
| G199E | 2.2 | CAP-domain - VI-domain |
| I200A | 2.2 | CAP-domain - VI-domain |
| I200V | 4.3 | CAP-domain - VI-domain |
| H203N | 2.2 | CAP-domain - VI-domain |
| Q205K | 2.2 | CAP-domain - VI-domain |
| S173C | 1.5 | CAP-domain - VI-domain |
| G185R/A188N | 7.3 | CAP-domain - VI-domain - CAP-loop |
| G185S/A188R | 6.9 | CAP-domain - VI-domain - CAP-loop |
| G185R/A186R/A188H/S189D/P190H/M191D | 15.8 | CAP-domain - VI-domain - CAP-loop |
| V160A/G185R/A188N/G199E/I200A/H203N/Q205K | 17.0 | CAP-domain - VI-domain - CAP-loop |
| V160A/G185S/A188R/G199E/I200A/H203N/Q205K | 17.0 | CAP-domain - VI-domain - CAP-loop |
| V160A/G199E/I200A/H203N/Q205K | 13.9 | CAP-domain - VI-domain |
| V160A/G185R/A186R/A188H/G199E/I200V/H203N/Q205K | 17.3 | CAP-domain - VI-domain - CAP-loop |

FIGURE 3B:

| Modification(s) of SEQ ID NO: 6 | Increase in T(50%) (%) | Region |
|---|---|---|
| F183Y | 2.3 | CAP-domain - VI-domain |
| V197C | 10.3 | CAP-domain - VI-domain |
| F183Y/V197C | 21.8 | CAP-domain - VI-domain |

FIGURE 4:

| Modification(s) of SEQ ID NO: 1 | Residual activity (%) | Region |
|---|---|---|
| V160A | 4.3 | CAP-domain - VI-domain |
| G185R | 6.2 | CAP-domain - VI-domain - CAP-loop |
| G185S | 6.5 | CAP-domain - VI-domain - CAP-loop |
| A186P | 7.9 | CAP-domain - VI-domain - CAP-loop |
| A186R | 7.9 | CAP-domain - VI-domain - CAP-loop |
| A188D | 6.5 | CAP-domain - VI-domain - CAP-loop |
| A188H | 7.3 | CAP-domain - VI-domain - CAP-loop |
| A188N | 7.0 | CAP-domain - VI-domain - CAP-loop |
| A188G | 6.8 | CAP-domain - VI-domain - CAP-loop |
| A188R | 6.7 | CAP-domain - VI-domain - CAP-loop |
| S189D | 6.4 | CAP-domain - VI-domain - CAP-loop |
| P190H | 7.0 | CAP-domain - VI-domain - CAP-loop |
| G199E | 4.2 | CAP-domain - VI-domain |
| I200A | 5.0 | CAP-domain - VI-domain |
| I200V | 5.4 | CAP-domain - VI-domain |
| H203N | 4.9 | CAP-domain - VI-domain |
| Q205K | 4.7 | CAP-domain - VI-domain |
| G185R/A188N | 16.7 | CAP-domain - VI-domain - CAP-loop |
| G185S/A188R | 17.3 | CAP-domain - VI-domain - CAP-loop |
| G185R/A186R/A188H/S189D/P190H/M191D | 62.8 | CAP-domain - VI-domain - CAP-loop |
| V160A/G185R/A188N/G199E/I200A/H203N/Q205K | 65.9 | CAP-domain - VI-domain - CAP-loop |
| V160A/G185S/A188R/G199E/I200A/H203N/Q205K | 68.5 | CAP-domain - VI-domain - CAP-loop |
| V160A/G199E/I200A/H203N/Q205K | 16.1 | CAP-domain - VI-domain |
| V160A/G185R/A186R/A188H/G199E/I200V/H203N/Q205K | 49.4 | CAP-domain - VI-domain - CAP-loop |

FIGURE 5:

| Analyte | Retention time (min) | Precursor ion (m/z) | Product ions (m/z) | Time (ms) | Declustering potential (V) | Entrance potential (V) | Collision energy (eV) |
|---|---|---|---|---|---|---|---|
| HZEN | 16.0 | 335.2 | 161/149 | 20 | -100 | -10 | -34 |
| α-ZEL | 20.2 | 319.1 | 275.1/160 | 20 | -125 | -10 | -30 |
| ZEN | 20.9 | 317.1 | 175/131 | 20 | -120 | -10 | -42 |
| DHZEN | 15.6 | 291.1 | 161.1/149.1 | 20 | -100 | -10 | -25 |

FIGURE 6:

| Group | ZEN + α-ZEL (µg) | Change (%) | Group | ZEN + α-ZEL (µg) | Change (%) |
|---|---|---|---|---|---|
| Control | 23 | +4.5 | Control | 33 | +37.5 |
| 2.5 U/kg diet SEQ ID NO: 1 | 22 | - | 5 U/kg diet SEQ ID NO: 1 | 24 | - |
| 2.5 U/kg diet Variant A | 13 | -36.4 | 5 U/kg diet Variant A | 13 | -45.8 |
| 2.5 U/kg diet Variant B | 19 | -13.6 | 5 U/kg diet Variant B | 13 | -45.8 |
| Group | ZEN + α-ZEL (µg) | Change (%) | Group | ZEN + α-ZEL (µg) | Change (%) |
| Control | 27 | +22.7 | Control | 31 | +72.2 |
| 10 U/kg diet SEQ ID NO: 1 | 22 | - | 20 U/kg diet SEQ ID NO: 1 | 18 | - |
| 10 U/kg diet Variant A | 17 | -22.7 | 20 U/kg diet Variant A | 12 | -33.3 |
| 10 U/kg diet Variant B | 8 | -63.6 | 20 U/kg diet Variant B | 4 | -77.8 |

FIGURE 7:

| Group | ZEN + α-ZEL (ng/g) | Change (%) | Group | ZEN + α-ZEL (ng/g) | Change (%) |
|---|---|---|---|---|---|
| Control | 42 | +50.0 | Control | 79 | +12.9 |
| 2.5 U/kg diet SEQ ID NO: 1 | 28 | - | 5 U/kg diet SEQ ID NO: 1 | 70 | - |
| 2.5 U/kg diet Variant A | 14 | -50.0 | 5 U/kg diet Variant A | 49 | -30.0 |
| 2.5 U/kg diet Variant B | 22 | -21.4 | 5 U/kg diet Variant B | 57 | -18.6 |
| Group | ZEN + α-ZEL (ng/g) | Change (%) | Group | ZEN + α-ZEL (ng/g) | Change (%) |
| Control | 91 | +33.8 | Control | 60 | +57.9 |
| 10 U/kg diet SEQ ID NO: 1 | 68 | - | 20 U/kg diet SEQ ID NO: 1 | 38 | - |
| 10 U/kg diet Variant A | 36 | -47.1 | 20 U/kg diet Variant A | 17 | -55.3 |
| 10 U/kg diet Variant B | 39 | -42.7 | 20 U/kg diet Variant B | 29 | -23,7 |

FIGURE 8:

| Analyte | Retention time (min) | Precursor ion (m/z) | Product ions (m/z) | Time (ms) | Declustering potential (V) | Entrance potential (V) | Collision energy (eV) |
|---|---|---|---|---|---|---|---|
| HZEN | 7.94 | 335.2 | 161/149 | 20 | -100 | -10 | -34 |
| α-ZEL | 11.40 | 319.1 | 275.1/160 | 20 | -125 | -10 | -30 |
| ZEN | 13.04 | 317.1 | 175/131 | 20 | -120 | -10 | -42 |
| DHZEN | 7.67 | 291.1 | 161.1/149.1 | 20 | -100 | -10 | -25 |

FIGURE 9:

| Control | | 5 U/kg diet Variant B | | 10 U/kg diet Variant B | |
|---|---|---|---|---|---|
| ZEN (μg/kg) | Change (%) | ZEN (μg/kg) | Change (%) | ZEN (μg/kg) | Change (%) |
| 247 | - | 228 | -7.7 | 165 | -33.2 |
| 20 U/kg diet Variant B | | 40 U/kg diet Variant B | | 80 U/kg diet Variant B | |
| ZEN (μg/kg) | Change (%) | ZEN (μg/kg) | Change (%) | ZEN (μg/kg) | Change (%) |
| 133 | -46.2 | 46 | -81.4 | 33 | -86.6 |
| 160 U/kg diet Variant B | | | | | |
| ZEN (μg/kg) | Change (%) | | | | |
| 27 | -89 | | | | |

SEQUENCE LISTING

```
<160> NUMBER OF SEQ ID NOS: 11

<210> SEQ ID NO 1
<211> LENGTH: 309
<212> TYPE: PRT
<213> ORGANISM: Artificial Sequence
<220> FEATURE:
<223> OTHER INFORMATION: Alpha/beta hydrolase domain

<400> SEQUENCE: 1

Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
            20                  25                  30

Ala Gly Asp Pro Asp Arg Pro Ala Val Leu Leu Ile Pro Glu Gln Thr
        35                  40                  45

Gly Ser Trp Trp Ser Tyr Glu Glu Ala Met Gly Leu Leu Ser Glu His
    50                  55                  60

Phe His Val Tyr Ala Val Asp Leu Arg Gly Gln Gly Arg Ser Ser Trp
65                  70                  75                  80

Thr Pro Lys Arg Tyr Ser Leu Asp Asn Phe Gly Asn Asp Leu Val Arg
                85                  90                  95

Phe Ile Ala Leu Val Val Lys Arg Pro Val Val Val Ala Gly Asn Ser
            100                 105                 110

Ser Gly Gly Val Leu Ala Ala Trp Leu Ser Ala Tyr Ser Met Pro Gly
        115                 120                 125

Gln Leu Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Gly Asp
                165                 170                 175

Trp Glu Gly Phe Cys Arg Ala Ala Gly Ala Ser Ala Ser Pro Met Ala
            180                 185                 190

Arg Ser Phe Val Ala Asp Gly Ile Pro Gln His Leu Gln Glu Tyr Asp
        195                 200                 205

Pro Glu Trp Ala Arg Val Phe Tyr Glu Gly Thr Val Gly Leu Ser Cys
    210                 215                 220

Pro His Glu Arg Met Leu Gly Gln Val Lys Thr Pro Val Leu Leu Thr
225                 230                 235                 240

His His Met Arg Gly Ile Asp Pro Glu Thr Gly Asn Leu Leu Gly Ala
                245                 250                 255

Leu Ser Asp Glu Gln Ala Leu Arg Ala Arg Arg Leu Met Asp Ser Ala
            260                 265                 270

Gly Val Thr Val Asp Tyr Glu Ser Val Pro Asp Ala Ser His Met Met
        275                 280                 285

His Gln Ser Ala Pro Ala Arg Tyr Val Glu Ile Phe Thr Arg Trp Ala
    290                 295                 300

Ala Ala Leu Ala Pro
```

<210> SEQ ID NO 2
<211> LENGTH: 308
<212> TYPE: PRT
<213> ORGANISM: Artificial Sequence
<220> FEATURE:
<223> OTHER INFORMATION: Alpha/beta hydrolase domain

<400> SEQUENCE: 2

```
Met Ala Asp Pro Ala Gln Arg Asp Val Tyr Val Pro His Ala Tyr Pro
1               5                   10                  15

Glu Lys Gln Ala Asp Leu Gly Glu Ile Thr Met Asn Tyr Ala Glu Ala
            20                  25                  30

Gly Glu Pro Asp Met Pro Ala Val Leu Leu Ile Pro Glu Gln Thr Gly
        35                  40                  45

Ser Trp Trp Gly Tyr Glu Glu Ala Met Gly Leu Leu Ala Glu Asn Phe
    50                  55                  60

His Val Tyr Ala Val Asp Leu Arg Gly Gln Gly Arg Ser Ser Trp Ala
65                  70                  75                  80

Pro Lys Arg Tyr Ser Leu Asp Asn Phe Gly Asn Asp Leu Val Arg Phe
                85                  90                  95

Ile Ala Leu Val Val Lys Arg Pro Val Ile Val Ala Gly Asn Ser Ser
            100                 105                 110

Gly Gly Val Leu Ala Ala Trp Leu Ser Ala Tyr Ser Met Pro Gly Gln
        115                 120                 125

Val Arg Gly Ala Leu Cys Glu Asp Ala Pro Phe Phe Ala Ser Glu Leu
    130                 135                 140

Val Thr Thr Cys Gly His Ser Ile Arg Gln Ala Ala Gly Pro Met Phe
145                 150                 155                 160

Glu Leu Phe Arg Thr Tyr Leu Gly Asp Gln Trp Ser Val Gly Asp Trp
                165                 170                 175

Thr Gly Tyr Cys Arg Ala Ala Asp Ala Ser Ser Ser Pro Met Ala Arg
            180                 185                 190

Tyr Phe Val Ala Asp Glu Ile Pro Gln His Met Arg Glu Tyr Asp Pro
        195                 200                 205

Glu Trp Ala Arg Ala Phe Trp Glu Gly Thr Val Ala Leu His Cys Pro
    210                 215                 220

His Glu Gln Leu Leu Thr Gln Val Lys Thr Pro Val Leu Leu Thr His
225                 230                 235                 240

His Met Arg Asp Ile Asp Pro Asp Thr Gly His Leu Val Gly Ala Leu
                245                 250                 255

Ser Asp Glu Gln Ala Ala Arg Ala Arg Leu Leu Met Glu Ser Ala Gly
            260                 265                 270

Val Lys Val Asp Tyr Ala Ser Val Pro Asp Ala Leu His Met Met His
        275                 280                 285

Gln Phe Asp Pro Pro Arg Tyr Val Glu Ile Phe Thr Gln Trp Ala Ala
    290                 295                 300

Thr Leu Ala Ala
305
```

<210> SEQ ID NO 3
<211> LENGTH: 309
<212> TYPE: PRT
<213> ORGANISM: Artificial Sequence
<220> FEATURE:
<223> OTHER INFORMATION: Alpha/beta hydrolase domain

<400> SEQUENCE: 3

```
Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
            20                  25                  30

Ala Gly Asp Pro Gly Arg Pro Ala Val Leu Leu Ile Pro Glu Gln Thr
        35                  40                  45

Gly Ser Trp Trp Ser Tyr Glu Glu Ala Met Gly Leu Leu Ala Glu His
    50                  55                  60

Phe His Val Tyr Ala Val Asp Leu Arg Gly Gln Gly Arg Ser Ser Trp
65                  70                  75                  80

Thr Pro Lys Arg Tyr Ser Leu Asp Asn Phe Gly Asn Asp Leu Val Arg
                85                  90                  95

Phe Ile Ala Leu Val Val Arg Arg Pro Val Val Ala Gly Asn Ser
            100                 105                 110

Ser Gly Gly Val Leu Ala Ala Trp Leu Ser Ala Tyr Ser Met Pro Gly
        115                 120                 125

Gln Ile Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Gly Asp
                165                 170                 175

Trp Glu Gly Phe Arg Ser Ala Ala Asp Ala Ser Ala Ser Pro Met Ala
            180                 185                 190

Arg Ser Phe Val Ala Asp Thr Ile Pro Gln His Leu Lys Glu Tyr Asp
        195                 200                 205

Pro Glu Trp Ala Arg Ala Phe Tyr Glu Gly Thr Val Gly Leu Asn Cys
    210                 215                 220

Pro His Glu Arg Met Leu Asn Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Val Arg Arg Leu Met Glu Ser Ala
            260                 265                 270

Gly Val Lys Val Asp Tyr Glu Ser Val Pro Asp Ala Ser His Met Met
        275                 280                 285

His Gln Ser Asp Pro Ala Arg Tyr Ala Glu Ile Leu Thr Pro Trp Thr
    290                 295                 300

Ala Ala Leu Ala Pro
305
```

<210> SEQ ID NO 4
<211> LENGTH: 309
<212> TYPE: PRT
<213> ORGANISM: Artificial Sequence
<220> FEATURE:
<223> OTHER INFORMATION: Alpha/beta hydrolase domain

<400> SEQUENCE: 4

```
Met Val Thr Ser Pro Ala Leu Arg Asp Val His Val Pro His Ala Tyr
1               5                   10                  15

Pro Glu Gln Gln Val Asp Leu Gly Glu Ile Thr Met Asn Tyr Ala Glu
            20                  25                  30
```

Ala Gly Asp Pro Asp Arg Pro Ala Val Leu Leu Ile Pro Glu Gln Thr
            35                  40                  45

Gly Ser Trp Trp Ser Tyr Glu Glu Ala Met Gly Leu Leu Ala Glu His
    50                  55                  60

Phe His Val Tyr Ala Val Asp Leu Arg Gly Gln Gly Arg Ser Ser Trp
 65                  70                  75                  80

Thr Pro Lys Arg Tyr Ser Leu Asp Asn Phe Gly Asn Asp Leu Val Arg
                85                  90                  95

Phe Ile Ala Leu Val Val Lys Arg Pro Val Val Ala Gly Asn Ser
                100                 105                 110

Ser Gly Gly Val Leu Ala Ala Trp Leu Ser Ala Tyr Ser Met Pro Gly
            115                 120                 125

Gln Leu Arg Gly Val Leu Cys Glu Asp Pro Pro Phe Phe Ala Ser Glu
        130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Ser Asp
                165                 170                 175

Trp Glu Gly Phe Cys Arg Ala Ala Gly Ala Ser Ala Ser Pro Met Ala
                180                 185                 190

Arg Ser Phe Val Ala Asp Gly Ile Pro Gln His Leu Lys Glu Tyr Asp
            195                 200                 205

Pro Glu Trp Ala Arg Ala Phe His Glu Gly Thr Val Gly Leu Asn Cys
        210                 215                 220

Pro His Glu Arg Met Leu Gly Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Ala Arg Leu Leu Met Glu Ser Ala
                260                 265                 270

Gly Val Arg Val Asp Tyr Glu Ser Val Pro Asp Ala Ser His Met Met
            275                 280                 285

His Gln Ser Asp Pro Ala Arg Tyr Ala Glu Ile Phe Thr Arg Trp Ala
        290                 295                 300

Ala Ala Leu Ala Pro
305

<210> SEQ ID NO 5
<211> LENGTH: 309
<212> TYPE: PRT
<213> ORGANISM: Artificial Sequence
<220> FEATURE:
<223> OTHER INFORMATION: Alpha/beta hydrolase domain

<400> SEQUENCE: 5

Met Val Thr Ser Pro Ala Leu Arg Asp Val His Val Pro His Ala Tyr
 1               5                  10                  15

Pro Glu Gln Gln Val Asp Leu Gly Glu Ile Thr Met Asn Tyr Ala Glu
                20                  25                  30

Ala Gly Asp Pro Gly Arg Pro Ala Val Leu Leu Ile Pro Glu Gln Thr
            35                  40                  45

Gly Ser Trp Trp Ser Tyr Glu Glu Ala Met Gly Leu Leu Ala Glu His
    50                  55                  60

Phe His Val Tyr Ala Val Asp Leu Arg Gly Gln Gly Arg Ser Ser Trp
 65                  70                  75                  80

-continued

```
Thr Pro Lys Arg Tyr Ser Leu Asp Asn Phe Gly Asn Asp Leu Val Arg
                85                  90                  95

Phe Met Ala Leu Val Val Arg Arg Pro Val Val Ala Gly Asn Ser
            100                 105                 110

Ser Gly Gly Val Leu Ala Ala Trp Leu Ser Ala Tyr Ser Met Pro Gly
        115                 120                 125

Gln Ile Arg Gly Val Leu Cys Glu Asp Pro Pro Phe Phe Ala Ser Glu
    130                 135                 140

Leu Val Pro Ala His Gly His Ser Val Arg Gln Gly Ala Gly Pro Val
145                 150                 155                 160

Phe Glu Leu Phe Arg Thr Tyr Leu Gly Asp Gln Trp Ser Val Gly Asp
                165                 170                 175

Trp Glu Gly Phe Arg Ser Ala Ala Gly Ala Ser Ala Ser Pro Met Ala
            180                 185                 190

Arg Ser Phe Val Ala Asp Thr Ile Pro Gln His Leu Lys Glu Tyr Asp
        195                 200                 205

Pro Glu Trp Ala Arg Ala Phe Tyr Glu Gly Thr Val Gly Leu Asn Cys
    210                 215                 220

Pro His Glu Arg Met Leu Asn Arg Val Asn Thr Pro Val Leu Leu Thr
225                 230                 235                 240

His His Met Arg Gly Thr Asp Pro Glu Thr Gly Asn Leu Leu Gly Ala
                245                 250                 255

Leu Ser Asp Glu Gln Ala Ala Gln Ala Arg Arg Leu Met Glu Ser Ala
            260                 265                 270

Gly Val Lys Val Asp Tyr Glu Ser Val Pro Ala Ser His Met Met
        275                 280                 285

His Gln Ser Asp Pro Ala Arg Tyr Ala Glu Ile Leu Thr Pro Trp Ala
    290                 295                 300

Ala Ala Leu Ala Pro
305
```

<210> SEQ ID NO 6
<211> LENGTH: 328
<212> TYPE: PRT
<213> ORGANISM: Artificial Sequence
<220> FEATURE:
<223> OTHER INFORMATION: Alpha/beta hydrolase domain

<400> SEQUENCE: 6

```
Met Ala Glu Glu Gly Thr Arg Ser Glu Ala Ala Asp Ala Ala Thr Gln
1               5                   10                  15

Ala Arg Gln Leu Pro Asp Ser Arg Asn Ile Phe Val Ser His Arg Phe
            20                  25                  30

Pro Glu Arg Gln Val Asp Leu Gly Glu Val Val Met Asn Phe Ala Glu
        35                  40                  45

Ala Gly Ser Pro Asp Asn Pro Ala Leu Leu Leu Pro Glu Gln Thr
    50                  55                  60

Gly Ser Trp Trp Ser Tyr Glu Pro Val Met Gly Leu Leu Ala Glu Asn
65                  70                  75                  80

Phe His Val Phe Ala Val Asp Ile Arg Gly Gln Gly Arg Ser Thr Trp
                85                  90                  95

Thr Pro Arg Arg Tyr Ser Leu Asp Asn Phe Gly Asn Asp Leu Val Arg
            100                 105                 110

Phe Ile Ala Leu Val Ile Lys Arg Pro Val Val Ala Gly Asn Ser
        115                 120                 125
```

```
Ser Gly Gly Leu Leu Ala Ala Trp Leu Ser Ala Tyr Ala Met Pro Gly
    130                 135                 140

Gln Ile Arg Ala Ala Leu Cys Glu Asp Ala Pro Phe Phe Ala Ser Glu
145                 150                 155                 160

Leu Val Pro Ala Tyr Gly His Ser Val Leu Gln Ala Ala Gly Pro Ala
                165                 170                 175

Phe Glu Leu Tyr Arg Asp Phe Leu Gly Asp Gln Trp Ser Ile Gly Asp
                180                 185                 190

Trp Lys Gly Phe Val Glu Ala Ala Lys Ala Ser Pro Ala Lys Ala Met
            195                 200                 205

Gln Leu Phe Pro Thr Pro Asp Glu Ala Pro Gln Asn Leu Lys Glu Tyr
210                 215                 220

Asp Pro Glu Trp Gly Arg Ala Phe Phe Glu Gly Thr Val Ala Leu His
225                 230                 235                 240

Cys Pro His Asp Arg Met Leu Ser Gln Val Lys Thr Pro Ile Leu Ile
                245                 250                 255

Thr His His Ala Arg Thr Ile Asp Pro Glu Thr Gly Glu Leu Leu Gly
                260                 265                 270

Ala Leu Ser Asp Leu Gln Ala Glu His Ala Gln Asp Ile Ile Arg Ser
            275                 280                 285

Ala Gly Val Arg Val Asp Tyr Gln Ser His Pro Asp Ala Leu His Met
        290                 295                 300

Met His Leu Phe Asp Pro Ala Arg Tyr Ala Glu Ile Leu Thr Ser Trp
305                 310                 315                 320

Ser Ala Thr Leu Pro Ala Asn Asp
                325

<210> SEQ ID NO 7
<211> LENGTH: 5
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
<223> OTHER INFORMATION: X is any amino acid

<400> SEQUENCE: 7

Gln Xaa Ala Gly Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Motif

<400> SEQUENCE: 8

Glu Tyr Asp Pro Glu
1               5

<210> SEQ ID NO 9
<211> LENGTH: 6
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (2)..(2)
```

```
<223> OTHER INFORMATION: X is F or Y
<220> FEATURE:
<221> NAME/KEY: MISC_FEATURE
<222> LOCATION: (3)..(4)
<223> OTHER INFORMATION: X is any amino acid

<400> SEQUENCE: 9

Gly Xaa Xaa Xaa Ala Ala
1               5

<210> SEQ ID NO 10
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: MISC_FEATURE
<222> LOCATION: (3)..(3)
<223> OTHER INFORMATION: X is any amino acid

<400> SEQUENCE: 10

Ala Arg Xaa Phe
1

<210> SEQ ID NO 11
<211> LENGTH: 4
<212> TYPE: PRT
<213> ORGANISM: Artificial Sequence
<220> FEATURE:
<223> OTHER INFORMATION: Motif

<400> SEQUENCE: 11

Gln Leu Phe Pro
1
```

MEANS AND METHODS FOR CLEAVAGE OF ZEARALENONE

PRIORITY CLAIM

This application claims priority to International Application No. PCT/EP2019/070434, filed Jul. 30, 2019, which claims priority to European Application No. 18186532.0, filed Jul. 31, 2018, wherein the contents of said applications are incorporated herein by reference in their entireties. Also, the entire contents of the ASCII text file entitled "IPM0109US_Sequence_Listing.txt" created on Jan. 25, 2021, having a size of 18 kilobytes is incorporated herein by reference.

TECHNICAL FIELD OF THE INVENTION

The present invention relates to a method for increasing the stability of an α/β-hydrolase. In addition, the present invention relates to an α/β-hydrolase obtainable by the method of the present invention. Also provided are α/β-hydrolases having a decreased grand average of hydropathy (GRAVY) value and/or comprising specific mutations. In addition, the present invention concerns a use of an α/β-hydrolase of the present invention for degrading zearalenone (ZEN).

DESCRIPTION

Mycotoxins are secondary metabolites produced by filamentous fungi. An important representative of mycotoxins is zearalenone (ZEN), which was previously known as F-2 toxin, which is produced by a variety of *Fusarium* fungi and can be found throughout the world. These fungi infest cultivated plants, among others, such as various types of grain, wherein the fungal infestation usually occurs before the harvest when the growth of the fungi and/or the mycotoxin production may take place before storage or may even take place after harvest, either prior to storage or under improper storage conditions. The Food and Agriculture Organization of the United Nations (FAO) has estimated that 25% of agricultural products throughout the world are contaminated with mycotoxins, thus resulting in substantial economic losses. In an international study spanning 8 years, a total of 19,757 samples was analyzed from January 2004 to December 2011; 72% of them testing positive for at least one mycotoxin, 39% were found to be co-contaminated, and 37% testing positive for ZEN (Schatzmayr and Streit (2013) 'Global occurrence of mycotoxins in the food and feed chain: Facts and figures.' World Mycotoxin Journal 6(3): 213-222). ZEN has been found in all regions of the world and in all types of grain and feed crops tested, such as corn, soy flour, wheat, wheat bran, DDGS (dried distillers grains with solubles) as well as in finished animal feed mixtures with an incidence of up to 100%.

ZEN binds to the estrogen receptor and can cause hormonal disruptions, being absorbed immediately after oral ingestion and converted by mammals into the two stereoisomeric metabolites α-zearalenol (α-ZEL) and/or β-zearalenol (β-ZEL). For example, α-ZEL but also α-zearalanol (α-ZAL) and/or zearalanone (ZAN) have a much stronger estrogenic effect than ZEN. Although conjugated ZEN derivatives have a lower estrogenic activity than ZEN itself, ZEN can be released again from these conjugated ZEN derivatives in the digestive tract and thereby regain its full estrogenic activity.

ZEN has an oral LD50 of up to 20,000 mg/kg body weight, subacute and/or subchronic toxic effects such as teratogenic, carcinogenic, estrogenic and immunosuppressant effects may occur in animals or humans with prolonged exposure. Feed contaminated with ZEN leads to developmental disorders in mammalian animals. Pigs and particularly piglets are extremely sensitive to ZEN. ZEN concentrations of more than 0.5 ppm in feed result in developmental disorders, and concentrations of more than 1.5 ppm can result in hyperestrogenicity in pigs. In cattle, concentrations of 12 ppm ZEN can cause spontaneous abortions.

Since ZEN is absorbed rapidly through the mucous membranes, in particular through the gastric mucosa as well as the oral mucosa, immediate and quantitative deactivation is essential. Already 30 minutes after oral administration, ZEN can be detected in the bloodstream. Because of the harmful effects of ZEN, the European Union has binding upper limits for ZEN in foodstuffs as well as recommendations for upper limits for ZEN in animal feed products (EC No. 1881/2006).

The primary strategy for reducing ZEN contamination of foods and animal feed products is to restrict the growth of fungi, for example by maintaining "good agricultural practice". This includes, among other things, ensuring that the seed is free of pests and fungal infestation or that agricultural waste products are removed from the field promptly. In addition, fungal growth in the field can be reduced by the use of fungicides. After the harvest, the harvested material should be stored at a residual moisture level of less than 15% and at a low temperature to prevent the growth of fungi. Likewise, material contaminated by fungal infestation should be removed before further processing. Despite this long list of preventive measures, even in regions with the highest agricultural standards such as North America and Central Europe, up to 37% of the tested corn samples were found contaminated with ZEN in the years 2004 to 2011 (Schatzmayr and Streit (2013)).

In order to counteract the above described problems and defects, it was necessary to develop further α/β-hydrolases capable of detoxifying ZEN and suited for use as a food or feed additive or a food or feed product.

The solution of the present invention is described in the following, exemplified in the examples, illustrated in the Figures and reflected in the claims.

The present invention relates to a method for increasing the stability of an α/β-hydrolase, which α/β-hydrolase comprises a sequence corresponding to positions 145 to 218 of SEQ ID NO: 1 or a sequence having 58% or more sequence identity to a sequence corresponding to positions 145 to 218 of SEQ ID NO: 1 (CAP-domain; 58% identity present to the CAP-domain of SEQ ID NO: 1), comprising substituting at least one amino acid at a position corresponding to position 160 to 205 of SEQ ID NO: 1, or at a position corresponding to position 159 to 204 of SEQ ID NO: 2, or at a position corresponding to position 160 to 205 of SEQ ID NO: 3, 4, or 5, or at a position corresponding to position 176 to 222 of SEQ ID NO: 6, wherein the amino acid(s) are substituted with an amino acid, which has a more negative hydropathy index than the substituted amino acid, wherein the hydropathy index is determined by the Kyte and Doolittle hydropathy index, thereby obtaining an α/β-hydrolase with increased stability.

In addition, the present invention relates to an α/β-hydrolase obtainable by the method of the present invention.

Also provided is an α/β-hydrolase having a polypeptide sequence comprising a sequence corresponding to positions 145 to 218 of SEQ ID NO: 1 or a sequence having more than 58% sequence identity to a sequence corresponding to positions 145 to 218 of SEQ ID NO: 1,
wherein the polypeptide sequence comprises at least one amino acid substitution
- at a position corresponding to position 160 to 205 of SEQ ID NO: 1, or
- at a position corresponding to position 159 to 204 of SEQ ID NO: 2, or
- at a position corresponding to position 160 to 205 of SEQ ID NO: 3, 4 or 5, or
- at a position corresponding to position 176 to 222 of SEQ ID NO: 6, wherein the α/β-hydrolase has a more negative grand average of hydropathy (GRAVY) value of at least 0.6% compared to the GRAVY value of an α/β-hydrolase having a polypeptide sequence of SEQ ID NO: 1.

The present invention also relates to an α/β-hydrolase having a polypeptide sequence comprising a sequence corresponding to positions 145 to 218 of SEQ ID NO: 1 or a sequence having more than 58% sequence identity to a sequence corresponding to positions 145 to 218 of SEQ ID NO: 1,
wherein the polypeptide sequence comprises at least one amino acid substitution
- at a position corresponding to position 185 to 191 of SEQ ID NO: 1, or
- at a position corresponding to position 184 to 190 of SEQ ID NO: 2 or
- at a position corresponding to a position 185 to 191 of SEQ ID NO: 3, 4 or 5, or
- at a position corresponding to a position of 201 to 208 of SEQ ID NO: 6, wherein the amino acid substitution is selected from V→A, G→R, G→S, A→P, A→R, A→D, A→H, A→N, A→G, S→D, P→H, M→D, G→E, I→A, I→V, H→N and Q→K and/or
wherein the amino acid(s) are substituted with an amino acid selected from P, R, D, H, G or N, preferably the amino acid is selected from R, D, H, G or N, more preferably the amino acid is selected from R or N.

The present invention also relates to an α/β-hydrolase having a polypeptide sequence comprising a sequence corresponding to positions 161 to 235 of SEQ ID NO: 6 or a sequence having more than 58% sequence identity to a sequence corresponding to positions 161 to 235 of SEQ ID NO: 6,
wherein the polypeptide sequence comprises at least one amino acid substitution
- at a position corresponding to position 160 to 205 of SEQ ID NO: 1, or
- at a position corresponding to position 159 to 204 of SEQ ID NO: 2, or
- at a position corresponding to position 160 to 205 of SEQ ID NO: 3, 4 or 5, or
- at a position corresponding to position 176 to 222 of SEQ ID NO: 6, wherein the α/β-hydrolase has a more negative GRAVY value of at least 0.6% compared to the GRAVY value of an α/β-hydrolase having a polypeptide sequence of SEQ ID NO: 6.

In addition, the present invention concerns a use of an α/β-hydrolase of the present invention for degrading ZEN.

Further, the present invention relates to a composition comprising an α/β-hydrolase of the present invention, preferably the composition is a food or feed additive or a food or feed product.

Also the present invention concerns an α/β-hydrolase or a composition of the present invention for use in the treatment or prophylaxis of a disease.

Further, the present invention relates to a kit comprising the α/β-hydrolase or the composition of the present invention.

The Figures show:

FIG. 1 Positions of CAP-domains, VI-domains and CAP-loops. Amino acid positions of CAP-domains, VI-domains and CAP-loops of SEQ ID NO: 1-6.

FIG. 2A-2G Different mutations in the VI-domain and/or in the CAP-loop and their influence on GRAVY values. 2A: Influence of modification(s) in the VI-domain of SEQ ID NO: 1 on GRAVY value of SEQ ID NO: 1 variants. 2B: Influence of modification(s) in the VI-domain of SEQ ID NO: 1 on GRAVY value of CAP-domains of SEQ ID NO: 1 variants. 2C: Influence of modification(s) in the VI-domain of SEQ ID NO: 1 on GRAVY value of VI-domains of SEQ ID NO: 1 variants. 2D: Influence of modification(s) in the CAP-loop of SEQ ID NO: 1 on GRAVY value of CAP-loop of SEQ ID NO: 1 variants. 2E: Influence of modification(s) in the VI-domain of SEQ ID NO: 6 on GRAVY value of SEQ ID NO: 6 variants. 2F: Influence of modification(s) in the VI-domain of SEQ ID NO: 6 on GRAVY value of VI-domains of SEQ ID NO: 6 variants. 2G: Influence of modification(s) in the VI-domain of SEQ ID NO: 6 on GRAVY value of VI-domains of SEQ ID NO: 6 variants.

FIG. 3A-3B Increase in temperature stability of ZEN-degrading polypeptides relative to polypeptide SEQ ID NO: 1 or SEQ ID NO: 6 in percent. 3A: Increase in temperature stability (T(50%)) of ZEN-degrading polypeptides relative to polypeptide SEQ ID NO: 1 in percent. 3B: Increase in temperature stability (T(50%)) of ZEN-degrading polypeptides relative to polypeptide SEQ ID NO: 6 in percent.

FIG. 4 Activities of ZEN-degrading polypeptide variants after incubation at pH 4.0 compared to activities after incubation at pH 7.5 (=pH stability). Residual activity of ZEN-degrading polypeptide variants after incubation at pH 4.0 compared to the same polypeptide variants after incubation at pH 7.5 in percent. The residual activity (pH stability) of the parent polypeptide SEQ ID NO: 1 is 2.5%.

FIG. 5 Selected reaction monitoring parameters on 6500 QTrap for analyses of samples from pig feeding trial. Analyses of samples from pig feeding trial were performed on an Agilent 1290 series UHPLC system coupled to a 6500 QTrap mass spectrometer.

Selected reaction monitoring parameters are shown. Product ions are given as quantifier/qualifier.

FIG. 6 Analysis results of urine samples from pig feeding trial compared to SEQ ID NO: 1. Combined amounts of ZEN plus α-ZEL in the urine sample of each group were determined on an Agilent 1290 series UHPLC system coupled to a 6500 QTrap mass spectrometer (average per group; n=3). The control group was fed a ZEN-containing diet, but no ZEN-degrading polypeptide. The groups SEQ ID NO: 1, Variant A and Variant B were fed the same diet as the control group, additionally containing the indicated ZEN-degrading polypeptide at either 2.5 U/kg, 5 U/kg, 10 U/kg or 20 U/kg diet. Changes in the amounts of ZEN plus α-ZEL in urine compared to SEQ ID NO: 1 are shown in percent FIG. 7 Analysis results of feces samples from pig feeding trial compared to SEQ ID NO: 1. Combined concentrations of ZEN plus α-ZEL per g freeze-dried feces were determined on an Agilent 1290 series UHPLC system coupled to a 6500 QTrap mass spectrometer (average per group; n=3). The control group was fed a ZEN-containing diet, but no ZEN-degrading polypeptide. The groups SEQ ID NO: 1, Variant A and Variant B were fed the same diet as the control group, additionally containing the indicated ZEN-degrading polypeptide at either 2.5 U/kg, 5 U/kg, 10 U/kg or 20 U/kg diet. Changes in the concentrations of ZEN plus α-ZEL in feces compared to SEQ ID NO: 1 are shown in percent.

FIG. 8 Selected reaction monitoring parameters on 6500 QTrap for analyses of samples from broiler feeding trial. Analyses of samples from broiler feeding trial were performed on an Agilent 1290 series UHPLC system coupled to a 6500 QTrap mass spectrometer. Selected reaction monitoring parameters are shown. Product ions are given as quantifier/qualifier.

FIG. 9 Analysis results of crop samples from broiler feeding trial compared to SEQ ID NO: 1. Concentrations of ZEN per kg lyophilized crop sample were determined on an Agilent 1290 series UHPLC system coupled to a 6500 QTrap mass spectrometer (average per group; n=8). The control group was fed a ZEN-containing diet, but no ZEN-degrading polypeptide. The other groups were fed the same diet as the control group, additionally containing the indicated amounts of enzymatic activity of the ZEN-degrading polypeptide variant B. Changes in the concentrations of ZEN in the crop compared to the control group are shown in percent.

It was surprisingly found that an α/β-hydrolase comprising a mutation as described herein in a specific region, namely the VI-domain and the CAP-loop, exhibits greater temperature stability and/or pH stability. Without wishing to be bound by theory, it is believed that the VI-domain and the CAP-loop play an important role for the enzyme activity e.g. for the entrance of the substrate to the active site of the enzyme. High flexibility of this part of the enzyme can have a positive impact on the activity, however, this flexibility can also have a negative impact on the stability.

The present inventors identified the CAP-domain of SEQ ID NO: 1 as amino acids from position 145 to 218, of SEQ ID NO: 2 from positions 144-217, from SEQ ID NO: 3, 4 and 5 from positions 145-218 and of SEQ ID NO: 6 from positions 161-235. Further the present inventors identified the VI-domain of SEQ ID NO: 1 from amino acid position 160 to 205, of SEQ ID NO: 2 from amino acid position 159-204, of SEQ ID NO: 3, 4 and 5 from amino acid position 160-205 and for SEQ ID NO: 6 from amino acid position 176-222. In particular, the combination of dynamics simulations with x-ray diffraction data of e.g. a variant of SEQ ID NO: 1 or 6 by Phenix ensemble refinement (https://www.phenix-online.org/; Burnley and Gros (2012) 'phenix.ensemble_refinement: a test study of apo and holo BACE1' Computational crystallography newsletter, volume 4, pp. 51-58) reflected a flexible loop by generating 65 structures. The region of SEQ ID NO: 1 defined by the amino acid positions 185 to 191, herein defined as CAP-loop, is part of this flexible loop (and by equivalent positions in SEQ ID NO: 2-6 as described herein as well).

Mutations as described herein introduced into the CAP-domain, in particular into the VI-domain as defined herein or more particularly into the CAP-loop as defined herein, provide for sufficient temperature stability without losing activity properties and/or pH stability so that such enzymes can be used in technological processes at elevated temperatures.

This is particularly important since thermal treatments such as pelletization for the production of hygienized products with reduced microbial load are commonly applied in food and feed industries.

The pelletization of feeds is a particularly widespread, standardized process to enhance flowability, reduce dust formation and to lower microbial load, in particular of salmonellae. During the pelletizing process, the commodity is usually moistened by hot steaming, heated and subsequently pressed through a matrix under pressure. Such a thermal treatment of enzymes or polypeptides often results in the reduction of their enzymatic activities and/or their irreversible denaturation.

Also, when applied in food or feed, enzymes are often subjected to inactivation by the conditions within the gastrointestinal tract of animals. Particularly environments of low pH can cause a temporary or permanent reduction or even elimination of the enzymatic activities of enzymes or polypeptides.

However, ZEN-degrading enzymes usually have low temperature stability and/or pH stability and thus cannot be admixed to feeds or foods as such. Therefore, the use of polypeptides or enzymes as additives for pelletizing foods or feeds constitutes a considerable technological challenge.

The α/β-hydrolases described herein have increased stability, especially with respect to temperature and/or pH stability, and are thus well suited for use in food and feed production processes.

Thus, the present invention relates to a method for increasing the stability of an α/β-hydrolase, which α/β-hydrolase comprises a sequence corresponding to positions 145 to 218 of SEQ ID NO: 1 or a sequence having 58% or more sequence identity to a sequence corresponding to positions 145 to 218 of SEQ ID NO: 1 (CAP-domain; 58% identity present to the CAP-domain of SEQ ID NO: 1), comprising substituting at least one amino acid
  at a position corresponding to position 160 to 205 of SEQ ID NO: 1, or
  at a position corresponding to position 159 to 204 of SEQ ID NO: 2, or
  at a position corresponding to position 160 to 205 of SEQ ID NO: 3, 4, or 5, or
  at a position corresponding to position 176 to 222 of SEQ ID NO: 6,
wherein the amino acid(s) are substituted with an amino acid, which has a more negative hydropathy index than the substituted amino acid,
wherein the hydropathy index is determined by the Kyte and Doolittle hydropathy index, thereby obtaining an α/β-hydrolase with increased stability, preferably the α/β-hydrolase has an increased stability compared to the α/β-hydrolase before substituting said amino acid(s) and/or has an increased stability compared to the α/β-hydrolase not comprising said amino acid substitution(s).

The present invention also relates to a method for increasing the stability of an α/β-hydrolase, which α/β-hydrolase comprises a sequence corresponding to positions 161 to 235 of SEQ ID NO: 6 or a sequence having 58% or more sequence identity to a sequence corresponding to positions 161 to 235 of SEQ ID NO: 6 (CAP-domain; 58% identity present to the CAP-domain of SEQ ID NO: 6), comprising substituting at least one amino acid
  at a position corresponding to position 160 to 205 of SEQ ID NO: 1, or
  at a position corresponding to position 159 to 204 of SEQ ID NO: 2, or at a position corresponding to position 160 to 205 of SEQ ID NO: 3, 4, or 5, or at a position corresponding to position 176 to 222 of SEQ ID NO: 6, wherein the amino acid(s) are substituted with an amino acid, which has a more negative hydropathy index than the substituted amino acid, wherein the hydropathy index is determined by the Kyte and Doolittle hydropathy index, thereby obtaining an α/β-hydrolase with increased stability, preferably the α/β-hydrolase has an increased stability compared to the α/β-hydrolase before substituting said amino acids and/or has an increased stability compared to the α/β-hydrolase not comprising said amino acid substitution(s).

An increased stability as used herein can mean that a α/β-hydrolase of the present invention has a higher stability than a α/β-hydrolase comprising a sequence corresponding to positions 145 to 218 of SEQ ID NO: 1 (as well as 3, 4, 5). Alternatively or additionally, an increased stability as used herein means that a W-hydrolase of the present invention has a higher stability than a α/β-hydrolase comprising a sequence corresponding to positions and/or comprises a sequence corresponding to positions 144 to 217 of SEQ ID NO: 2. Alternatively or additionally, an α/β-hydrolase comprises a sequence corresponding to positions 161 to 235 of SEQ ID NO: 6.

An increased stability as used herein can also mean that a α/β-hydrolase of the present invention has a higher stability than a α/β-hydrolase of SEQ ID NO: 1. Alternatively or additionally, an increased stability as used herein can also mean that a α/β-hydrolase of the present invention has a higher stability than a α/β-hydrolase of SEQ ID NO: 2. Alternatively or additionally, an increased stability as used herein can also mean that a α/β-hydrolase of the present invention has a higher stability than a α/β-hydrolase of SEQ ID NO: 6.

This includes that the α/β-hydrolase with increased stability e.g. obtained by the methods of the present invention or a α/β-hydrolase of the invention has an increased stability compared to the α/β-hydrolase not comprising the substitution(s) as disclosed herein. Likewise, the α/β-hydrolase with increased stability e.g. obtained by the methods of the present invention or a α/β-hydrolase of the invention has an increased stability compared to the α/β-hydrolase before substituting the amino acid(s) as disclosed herein.

The person skilled in the art knows various α/β-hydrolases, which are inter alia described in Lenfant et al. (2013) 'ESTHER, the database of the α/β-hydrolase fold superfamily of proteins: tools to explore diversity of functions' Nucleic Acids Research, Volume 41, Issue D1, D423-D429 and Mindrebo et al. (2016) 'Unveiling the functional diversity of the Alpha-Beta hydrolase fold in plants' Curr Opin Struct Biol. 233-246. In short, all α/β-hydrolases share the feature of a specific fold called α/β-fold (alpha/beta-fold). The α/β-hydrolase fold is common to a number of hydrolytic enzymes of widely differing phylogenetic origin and catalytic function. The core of each enzyme is an α/β-structure (rather than a barrel), containing 8 β-strands (b1-b8) connected by α-helices (aA-aF) (Ollis et al. (1992) 'The alpha/beta hydrolase fold' Protein Eng. 5(3):197-211). Therefore, an α/β-hydrolase as described herein can comprise an α/β-fold. An α/β-hydrolase as described herein preferably comprises the α/β-hydrolase core domain consisting of 8 β-strands (b1-b8) arranged to a central β-sheet and additionally comprises 6 crossover α-helices (aA-aF).

In most of the family members, the β-strands are in parallel orientation, but some have an inversion of the first strands, resulting in an antiparallel orientation. The prototype of enzymes in the fold has a catalytic triad composed of a nucleophilic residue located at the top of a γ-turn between the fifth β-strand and the following α-helix (the nucleophile elbow), an acidic amino acid residue (glutamic acid or aspartic acid) and a histidine residue. Some other members lack one or all of the catalytic residues. Some members are therefore inactive; some members are involved in surface recognition. An α/β-hydrolase as described herein preferably comprises the catalytic triad.

Members of different classes of α/β-hydrolases as well as their structural characteristics are inter alia described in Kourist et al. (2010) 'The alpha/beta-hydrolase fold 3DM database (ABHDB) as a tool for protein engineering.' Chembiochem. 11(12):1635-43).

As enzymes, α/β-hydrolases are often described to be responsible for the hydrolysis of ester and peptide bonds. However, α/β-hydrolases also participate in the breaking of carbon-carbon bonds, decarboxylation reactions and cofactor-independent dioxygenation of heteroaromatic rings. Thus, α/β-hydrolases can include catalytic members (enzymes) in this superfamily. Non-limiting examples are hydrolases (acetylcholinesterase, carboxylesterase, dienelactone hydrolase, lipase, cutinase, thioesterase, serine carboxypeptidase, proline iminopeptidase, proline oligopeptidase, epoxide hydrolase) along with enzymes that require activation of HCN, $H_2O_2$ or $O_2$ instead of $H_2O$ for the reaction mechanism (haloalkane dehalogenase, haloperoxidase, hydroxynitrile lyase). Non-catalytic members can include the neuroligins, glutactin, neurotactin, the C-terminal domain of thyroglobulin, yolk proteins, the CCG1-interacting-factor-B and dipeptidylaminopeptidase VI.

The ESTHER database gathers and annotates published information related to gene and protein sequences of this superfamily. Thus, the person skilled in the art can also obtain α/β-hydrolases from ESTHER (http://bioweb.supagro.inra.fr/ESTHER/general?what=index), a database of the α/β-hydrolase-fold superfamily of proteins.

The person skilled in the art can also determine if an α/β-hydrolase comprises a CAP-domain. One way to do this is described in the examples or as described below:

1. Search for an α/β-hydrolase within an online enzyme database or by comparing a given sequence with SEQ ID NO: 1-6.
2. Determination if the α/β-hydrolase contains a CAP-domain, a VI-domain or a CAP-loop, preferably by using the procedure described in example 2.
3. Determination if the α/β-hydrolase containing a CAP-domain, a VI-domain or a CAP-loop is able to hydrolyze ZEN, preferably by using the procedure described in example 4.

An α/β-hydrolase as used herein comprises a sequence corresponding to positions 145 to 218 of SEQ ID NO: 1 or a sequence having 58% or more sequence identity to a sequence corresponding to positions 145 to 218 of SEQ ID NO: 1 (CAP-domain). Thus, any α/β-hydrolase comprising this sequence is embraced by the term α/β-hydrolase. This sequence corresponds to the CAP-domain of the α/β-hydrolase of SEQ ID NO: 1.

Additionally or alternatively, an α/β-hydrolase as used herein can also comprise a sequence corresponding to positions 144 to 217 of SEQ ID NO: 2 or a sequence having 58% or more sequence identity to a sequence corresponding to positions 144 to 217 of SEQ ID NO: 2 (CAP-domain). Thus, any α/β-hydrolase comprising this sequence is embraced by the term α/β-hydrolase. This sequence corresponds to the CAP-domain of the α/β-hydrolase of SEQ ID NO: 2.

Additionally or alternatively, an α/β-hydrolase as used herein can also comprise a sequence corresponding to positions 145 to 218 of SEQ ID NO: 3, 4 or 5 or a sequence having 58% or more sequence identity to a sequence corresponding to positions 145 to 218 of SEQ ID NO: 3, 4 or 5 (CAP-domain). Thus, any α/β-hydrolase comprising this sequence is embraced by the term α/β-hydrolase. This sequence corresponds to the CAP-domain of the α/β-hydrolase of SEQ ID NO: 3, 4 or 5.

Additionally or alternatively, an α/β-hydrolase as used herein can also comprise a sequence corresponding to positions 161 to 235 of SEQ ID NO: 6 or a sequence having 58% or more sequence identity to a sequence corresponding to positions 161 to 235 of SEQ ID NO: 6 (CAP-domain). Thus, any α/β-hydrolase comprising this sequence is embraced by the term α/β-hydrolase. This sequence corresponds to the CAP-domain of the α/β-hydrolase of SEQ ID NO: 6.

For example, the α/β-hydrolase can comprise a sequence having at least 58%, 59%, 60%, 65%, 70%, 75%, 80%, 85%, 90%, 95%, 97%, 98%, 99% identity to a sequence of SEQ ID NO: 1. Additionally or alternatively, the α/β-hydrolase can comprise a sequence having at least 58%, 59%, 60%, 65%, 70%, 75%, 80%, 85%, 90%, 95%, 97%, 98%, 99% identity to a sequence of SEQ ID NO: 2. Additionally or alternatively, the α/β-hydrolase can comprise a sequence having at least 58%, 59%, 60%, 65%, 70%, 75%, 80%, 85%, 90%, 95%, 97%, 98%, 99% identity to a sequence of SEQ ID NO: 3, 4, and/or 5. Additionally or alternatively, the α/β-hydrolase can comprise a sequence having at least 58%, 59%, 60%, 65%, 70%, 75%, 80%, 85%, 90%, 95%, 97%, 98%, 99% identity to a sequence of SEQ ID NO: 6.

The term "polypeptide" when used herein means a peptide, a protein, or a polypeptide, which is used interchangeably and which encompasses amino acid chains of a given length, wherein the amino acid residues are linked by covalent peptide bonds. Also encompassed by the invention are amino acids other than the 20 proteinogenic amino acids of the standard genetic code known to a person skilled in the art, such as selenocysteine. Such polypeptides include any of SEQ ID NOs. 1-6.

The term polypeptide also refers to, and does not exclude, modifications of the polypeptide. Modifications include glycosylation, acetylation, acylation, phosphorylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination; see, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York (1983), pgs. 1-12; Seifter, Meth. Enzymol. 182 (1990); 626-646, Rattan, Ann. NY Acad. Sci. 663 (1992); 48-62.

In accordance with the present invention, the term "identical" or "percent identity" in the context of two or more polypeptide sequences such as SEQ ID NO: 1-6 refers to two or more sequences or subsequences that are the same, or that have a specified percentage of nucleotides that are the same (e.g., at least 85%, 90%, 95%, 96%, 97%, 98% or 99% identity), when compared and aligned for maximum correspondence over a window of comparison, or over a designated region as measured using a sequence comparison algorithm as known in the art, or by manual alignment and visual inspection. Sequences having, for example, 80% to 95% or greater sequence identity are considered to be substantially identical. Such a definition also applies to the complement of a test sequence. Those having skill in the art will know how to determine percent identity between/among sequences using, for example, algorithms such as those based on CLUSTALW computer program (Thompson Nucl. Acids Res. 2 (1994), 4673-4680) or FASTDB (Brutlag Comp. App. Biosci. 6 (1990), 237-245), as known in the art.

Also available to those having skills in this art are the BLAST and BLAST 2.6 algorithms (Altschul Nucl. Acids Res. 25 (1977), 3389-3402). The BLASTP program for amino acid sequences uses as defaults a word size (W) of 6, an expect threshold of 10, and a comparison of both strands. Furthermore, the BLOSUM62 scoring matrix (Henikoff Proc. Natl. Acad. Sci., USA, 89, (1989), 10915; Henikoff and Henikoff (1992) 'Amino acid substitution matrices from protein blocks.' Proc Natl Acad Sci USA. 1992 Nov. 15; 89(22):10915-9) can be used.

For example, BLAST2.6, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments.

A 'CAP-domain' as used herein relates to the CAP-domain of α/β-hydrolases, which is e.g. described in FIG. 1 of Kourist et al. (2010) 'The alpha/beta-hydrolase fold 3DM database (ABHDB) as a tool for protein engineering.' Chembiochem. 11(12):1635-43, or in Carr and Ollis (2009) 'a/p Hydrolase Fold: An Update.' Protein & Peptide Letters, 2009, 16(10):1137-1148. It is also envisioned that a CAP-domain can be located within the excursion between a β-sheet and an α-helix, e.g. between b6 and aD of the α/β-hydrolase e.g. as described by Ollis et al. (1992) 'The alpha/beta hydrolase fold' Protein Eng. 5(3):197-211. For example, a CAP-domain can begin shortly after the C-terminal end of the b6 β-strand of the α/β-hydrolase core domain, and can span until the N-terminal start of the aD α-helix of the α/β-hydrolase core domain. It is envisioned that a CAP-domain may comprise α-helices. However, the CAP-domain may also comprise β-sheets or other protein structures.

The method of the present invention requires substituting at least one amino acid
    at a position corresponding to position 160 to 205 of SEQ ID NO: 1, or
    at a position corresponding to position 159 to 204 of SEQ ID NO: 2, or
    at a position corresponding to position 160 to 205 of SEQ ID NO: 3, 4, or 5, or
    at a position corresponding to position 176 to 222 of SEQ ID NO: 6 of the α/β-hydrolase.
These positions are all located within a VI-domain.

As used herein the 'VI-domain' is a part of the CAP-domain. Thus, the CAP-domain comprises the VI-domain. This VI-domain can start with the first amino acid after the QXAGP motif (SEQ ID NO: 7) present in the CAP-domain and can span until the last amino acid before the EYDPE motif (SEQ ID NO: 8), whereas the EYDPE motif is not part of the VI-domain. These motifs are underlined in the sequences depicted in Table 2 herein.

For example, the VI-domain can comprise a sequence that corresponds to position 160 to 205 of SEQ ID NO: 1 or a sequence having at least 58%, 59%, 60%, 65%, 70%, 75%, 80%, 85%, 90%, 95%, 97%, 98%, 99% identity to a sequence that corresponds to position 160 to 205 of SEQ ID NO: 1. Additionally or alternatively, the VI-domain can comprise a sequence that corresponds to positions 159 to 204 of SEQ ID NO: 2 or a sequence having at least 58%, 59%, 60%, 65%, 70%, 75%, 80%, 85%, 90%, 95%, 97%, 98%, 99% identity to a sequence that corresponds to position 159 to 204 of SEQ ID NO: 2. Additionally or alternatively, the VI-domain can comprise a sequence that corresponds to positions 160 to 205 of SEQ ID NO: 3, 4 and/or 5 or a sequence having at least 58%, 59%, 60%, 65%, 70%, 75%, 80%, 85%, 90%, 95%, 97%, 98%, 99% identity to a sequence that corresponds to positions 160 to 205 of SEQ ID NO: 3, 4 and/or 5. Additionally or alternatively, the VI-domain can comprise a sequence that corresponds to positions 176 to 222 of SEQ ID NO: 6 or a sequence having at least 58%, 59%, 60%, 65%, 70%, 75%, 80%, 85%, 90%, 95%, 97%, 98%, 99% identity to a sequence that corresponds to positions 176 to 222 of SEQ ID NO: 6.

The term "position" when used in accordance with the present invention means the position of an amino acid within an amino acid sequence depicted herein. The term "corresponding" as used herein also includes that a position is not only determined by the number of the preceding amino acids. The position of a given amino acid in accordance with the present invention, which may be substituted, may vary due to deletions or additional amino acids or may be substituted, may vary due to deletion or addition of amino acids elsewhere in a (mutant or wild-type) α/β-hydrolase.

Thus, under a "corresponding position" in accordance with the present invention it is preferably to be understood that amino acids may differ in the indicated number but may still have similar neighbouring amino acids. Said amino acids which may be exchanged, deleted or added are also comprised by the term "corresponding position". Specifically, the skilled person may, when aligning the reference sequence (subject sequence) for example any one of SEQ ID No: 1-6, preferably SEQ ID NO: 1, with an amino acid sequence of interest (query sequence), for example, inspect a sequence of interest for the sequence of SEQ ID NO: 1 (or the corresponding amino acid sequence encoding this protein) when looking for the amino acid position as specified herein (i.e. a position corresponding to position 185 and/or 188 of the amino acid sequence shown in SEQ ID No: 1).

In the method of the present invention amino acid(s) are substituted with an amino acid, which has a more negative hydropathy index than the substituted amino acid, wherein the hydropathy index is determined by the Kyte and Doolittle hydropathy index.

As described herein an "amino acid substitution" means a replacement of an amino acid relative to a corresponding position of an identified SEQ ID NO e.g. any one of the herein indicated positions of SEQ ID NO: 1-6. For example, in one embodiment the replacement is an amino acid substitution of an amino acid relative to a position corresponding to position 160 to 205 of SEQ ID NO: 1.

The 'hydropathy index' also referred to as 'hydropathy value' herein is a number representing the hydrophobic or hydrophilic properties of the sidechain of an amino acid. In particular, with the hydropathy index each amino acid has been assigned a value reflecting its relative hydropathy. Thus, the hydropathy of an amino acid can be determined by the hydropathy index. This hydropathy index of an amino acid was proposed by Jack Kyte and Russell F. Doolittle (Kyte and Doolittle (1983) "A simple method for displaying the hydropathic character of a protein". J. Mol. Biol. 157 (1): 105-32). The amino acids with the least negative hydropathy index are isoleucine (4.5) and valine (4.2). According to Kyte and Doolittle the amino acids with the most negative hydropathy index are arginine (−4.5) and lysine (−3.9). The hydropathy index is considered to be important in protein structure. Amino acids with a less negative hydropathy index tend to be internal (with regard to the protein's threedimensional shape) while amino acids with a more negative hydropathy index are more commonly found on the protein surface. The hydropathy index of Kyte and Doolittle has been summarized herein in Table 1:

TABLE 1

Hydropathy index of Kyte and Doolittle

| aa | aa | Hydropathy index (Kyte-Doolittle) |
|---|---|---|
| R | Arginine | −4.50 |
| K | Lysine | −3.90 |
| N | Asparagine | −3.50 |
| Q | Glutamine | −3.50 |
| D | Aspartic acid | −3.50 |
| E | Glutamic acid | −3.50 |
| H | Histidine | −3.20 |
| P | Proline | −1.60 |
| Y | Tyrosine | −1.30 |
| W | Tryptophan | −0.90 |
| S | Serine | −0.80 |
| T | Threonine | −0.70 |
| G | Glycine | −0.40 |
| A | Alanine | 1.80 |
| M | Methionine | 1.90 |
| C | Cysteine | 2.50 |
| F | Phenylalanine | 2.80 |
| L | Leucine | 3.80 |
| V | Valine | 4.20 |
| I | Isoleucine | 4.50 |

It is further envisioned that at least one, two, three, four, five, six, seven, eight, nine, ten, eleven, twelve or more amino acids are substituted.

The method also envisions substituting at least one amino acid
 at a position corresponding to position 185 to 191 of SEQ ID NO: 1, and/or
 at a position corresponding to position 184 to 190 of SEQ ID NO: 2 and/or
 at a position corresponding to position 185 to 191 of SEQ ID NO: 3, 4 or 5 and/or
 at a position corresponding to position 201 to 208 of SEQ ID NO: 6.

All these positions are located within the CAP-loop.

In this context it is noted that the CAP-domain and the VI-domain can further comprise a loop (sequence/domain). This 'loop' also referred to as 'CAP-loop' herein can begin after the first amino acid after the G(F/Y)XXAA (SEQ ID NO: 9) motif present in the VI-domain and can span until the last amino acid before the ARXF motif (SEQ ID NO: 10) (or the QLFP motif (SEQ ID NO: 11) for SEQ ID NO: 6), whereas the ARXF motif (or the QLFP motif for SEQ ID NO: 6) is not part of the CAP-loop. All these motifs have been underlined in Table 2 below.

For example, the CAP-loop can comprise a sequence that corresponds to position 185 to 191 of SEQ ID NO: 1 or a sequence having at least 58%, 59%, 60%, 65%, 70%, 75%, 80%, 85%, 90%, 95%, 97%, 98%, 99% identity to a sequence that corresponds to position 185 to 191 of SEQ ID NO: 1. Additionally or alternatively, the CAP-loop can comprise a sequence that corresponds to positions 184 to 190 of SEQ ID NO: 2 or a sequence having at least 58%, 59%, 60%, 65%, 70%, 75%, 80%, 85%, 90%, 95%, 97%, 98%, 99% identity to a sequence that corresponds to position 184 to 190 of SEQ ID NO: 2. Additionally or alternatively, the CAP-loop can comprise a sequence that corresponds to positions 185 to 191 of SEQ ID NO: 3, 4, and/or 5 or a sequence having at least 58%, 59%, 60%, 65%, 70%, 75%, 80%, 85%, 90%, 95%, 97%, 98%, 99% identity to a sequence that corresponds to positions 185 to 191 of SEQ ID NO: 3, 4, and/or 5. Additionally or alternatively, the CAP-loop can comprise a sequence that corresponds to positions 201 to 208 of SEQ ID NO: 6 or a sequence having at least 58%, 59%, 60%, 65%, 70%, 75%, 80%, 85%, 90%, 95%, 97%, 98%, 99% identity to a sequence that corresponds to positions 201 to 208 of SEQ ID NO: 6.

Thus the α/β-hydrolases as described herein can comprise a VI-domain and/or a CAP-loop as described herein.

It is also contemplated that the amino acid(s) are substituted with an amino acid selected from R, K, N, Q, D, E, H, P, Y, W, S, T, G, A, M, C, F, L or V.

It is further envisioned that the amino acid(s) are substituted with an amino acid selected from R, K, N, Q, D, E, H, P, Y, W, S, T or G.

It is also contemplated that the amino acid(s) are substituted with an amino acid selected from R, K, N, Q, D, E, H or P.

It is further envisioned that the amino acid(s) are substituted with an amino acid selected from R, K, D, Q, D, N, E, P, G, T, S or H.

It is also contemplated that the amino acid(s) are substituted with an amino acid selected from S, P, R, D, H, G or N. The amino acid(s) can also be substituted with an amino acid selected from R, D, H, G or N.

It is also contemplated that the amino acid(s) are substituted with an amino acid selected from P, S, R or H. The amino acid(s) can also be substituted with an amino acid selected from R or N.

It is further envisioned that the amino acid substitution is selected from one or more of V→A, G→R, G→S, A→P, A→R, A→D, A→H, A→N, A→G, S→D, P→H, M→D, G→E, I→A, I→V, H→N, Q→K, F→Y and/or V→C. The amino acid substitution can also be selected from one or more of V160A, G185R, G185S, A186P, A186R, A188D, A188H, A188N, A188G, A188R, S189D, P190H, M191D, G199E, I200A, I200V, H203N, Q205K, F183Y and/or V197C.

It is also envisioned that the amino acid substitution is selected from one or more of V→A, G→R, G→S, A→P, A→R, A→D, A→H, A→N, A→G, S→D, P→H, M→D, G→E, I→A, I→V, H→N and/or Q→K. The amino acid substitution can also be selected from one or more of V160A, G185R, G185S, A186P, A186R, A188D, A188H, A188N, A188G, A188R, S189D, P190H, M191D, G199E, I200A, I200V, H203N and/or Q205K.

The amino acid substitution can also be selected from G185R, A186R, A188R, A188D, A188H, A188N and/or M191D.

It is further envisioned that the amino acid(s) are substituted with an amino acid selected from R, D, H, G, N or P.

It is also contemplated that the method of the invention comprises substituting at least one amino acid
- at a position corresponding to position 185 to 191 of SEQ ID NO: 1, and/or
- at a position corresponding to position 184 to 190 of SEQ ID NO: 2 and/or
- at a position corresponding to position 185 to 191 of SEQ ID NO: 3, 4 or 5 and/or
- at a position corresponding to position 201 to 208 of SEQ ID NO: 6.

and wherein the amino acid(s) are substituted with an amino acid selected from R, D, H, G, N or P.

The present invention relates to a method for increasing the stability of an α/β-hydrolase. The increase in stability can be a decrease in GRAVY value, an increase in pH stability and/or an increase in temperature stability.

As used herein the 'GRAVY value' of a protein is a measure of its relative hydrophobicity or hydrophilicity. The two measures are combined in a hydropathy scale or hydropathy index. In accordance with Kyte and Doolittle (Kyte J, Doolittle RF (May 1983). "A simple method for displaying the hydropathic character of a protein". J. Mol. Biol. 157 (1): 105-32), the GRAVY value is calculated by adding the hydropathy value (hydropathy index, see Table 1 above) for each residue and dividing by the number of residues in the sequence. Thus, the GRAVY value can be calculated by the sum of the hydropathy values (indeces) of all amino acids divided by the number of amino acid residues in the sequence (in accordance with calculation of Kyte and Doolittle). As used herein the term 'temperature stability' refers to the property of enzymes to maintain their catalytic activities after temporary exposure to elevated temperatures. The temperature stability is determined by measuring and comparing the enzymatic activity of an enzyme or polypeptide solution before and after a 10-minute heat treatment or without heat treatment at identical, defined conditions.

In particular, the temperature stability can be measured as follows. The polypeptides are diluted with sample buffer (Teorell Stenhagen buffer at pH 7.5 (Stenhagen & Teorell. (1938) Nature 141, 415), containing 0.1 mg/ml bovine serum albumin) to a concentration of 0.001526923 U/ml and kept on ice until further use. Forty 50 µl aliquots of diluted polypeptide solution are transferred into the tubes of four 12-tube strips (e.g. from starlab) while omitting the first and the last tubes of each strip. The strips are sealed with 12-strip caps (e.g. from starlab). As positive controls, four 50 µl aliquots of diluted enzyme solution are transferred into four PCR tubes. All PCR tubes and strips are kept on ice until the temperature incubation step is started. As negative controls, four 50 µl aliquots of sample buffer are transferred into four PCR tubes. These tubes are stored at 25° C.

The four 12-tube strips are incubated in a pre-heated PCR cycler with a gradient function (e.g. Eppendorf Mastercycler gradient) at a chosen temperature+/−10° C. The temperature gradient (+/−10° C. of the chosen temperature) along the thermoblock of the PCR cycler is calculated automatically by the PCR cycler. The PCR tubes containing the positive controls are incubated on ice, those containing the negative controls are incubated at 25° C. After 0, 5, 10 and 20 minutes, one PCR strip and one negative control tube are transferred to be kept on ice until the end of the incubation, i.e. 20 min after start of the incubation. After all incubation steps are finished and all strips and tubes are on ice, the ZEN degradation assays are started.

The ZEN degradation assay buffer (Teorell Stenhagen buffer, pH 7.5 containing 0.1 mg/ml bovine serum albumin and 5.3 ppm ZEN) is prepared and 660 µl aliquots of assay buffer are transferred into 48 reaction tubes. The tubes are sealed and kept at 25° C. until the start of the ZEN degradation assays. For the degradation assays, 40 µl of each of the 40 temperature-treated sample from the PCR strips, 40 µl of each of the four negative controls and 40 µl of each of the four positive controls are added to the tubes containing the 660 µl assay buffer, hereby achieving a final ZEN concentration of 5 ppm in the assay reaction. Also, a final concentration of the polypeptides is hereby achieved to degrade ZEN efficiently (i.e. 90%-100% ZEN degradation) within three hours.

By adding either temperature-treated samples, positive or negative controls to the assay buffer, the degradation assay is started. The ZEN degradation reaction is incubated in a pre-warmed water bath at 37° C. Immediately after a degradation reaction is started, it is mixed by vortexing for about 2 seconds and a 0 h sample of 100 µl is transferred into a new reaction tube. Additional samples are drawn from the ZEN degradation assay reaction after 0.5, 1.0, 2.0 and 3.0 hours. As soon as a sample is drawn from the degradation reaction, the enzyme in this sample is heat-inactivated by incubation for 10 minutes at 99° C. Subsequently, the tube is centrifuged (2 minutes, 25° C., 14674×g) and 90 µl of the supernatant is transferred into a HPLC vial with insert. These HPLC vials are stored at 4° C. until HPLC-DAD measurement as described in Example 4.

Using the linear decrease in ZEN concentration as determined by HPLC-DAD analysis of the ZEN degradation samples, enzyme activities are calculated in Units per liter (U/l). One Unit is defined as the amount of enzymatic activity that degrades one pmol of ZEN in one minute under the conditions described. The residual activities after incubation at different temperatures for 0, 5, 10 and 20 minutes are calculated as follows: Enzymatic activity in a temperature-treated sample divided by the average of the enzymatic activities of the positive controls, multiplied by 100.

Temperature stability (T(50%)) is defined as the temperature at which the polypeptides have 50% residual activity after 10 minutes of incubation in comparison with the positive control. The following example serves for illustration: The parental enzyme has an enzymatic activity of 50 U/ml after a 10-minute incubation on ice and an activity of 25 U/ml after a 10-minute incubation at 59.3° C., thus the T(50%) value is 59.3° C. If an enzyme variant has a T(50%) value of 61.0° C., the relative increase in the temperature stability (T(50%)) compared to the parental enzyme is 2.9%. This results from the difference between the two T(50%) values of 1.7° C., divided by the T(50%) value of the parental enzyme of 59.3° C., multiplied by 100.

The temperature stability as used herein is thus a measure for the resistance of an enzymatic activity towards inactivation upon temporary exposure to temperatures selected from a range between 20° C. and 85° C. The temperature at which the residual activity of the heat-treated enzyme after incubation for 10 minutes is 50% can be compared to the positive control. The increase in T(50%) of a polypeptide variant relative to its parent polypeptide is defined herein as a an increased temperature stability and can be indicated relatively as a percentage value or absolutely in degree Celsius.

The term 'pH stability' as used herein refers to the property of polypeptides to maintain their catalytic activities after temporary incubation at a certain pH and is thus reflected by the residual activity of the polypeptide after temporary incubation at a certain pH. The residual activity after incubation at a certain pH is determined by comparing the ZEN-degrading enzymatic activity of a polypeptide solution after a 60-minute incubation in buffers of different pH to the enzymatic activity in a solution of the same polypeptide after a 60-minute incubation in a buffer of pH 7.5. The pH stability is a measure for the resistance of enzymes towards temporary exposure to environments of a certain pH. An increase in pH stability is defined as the increase of the residual activity after incubation at pH 4.0 (=pH treatment) of a polypeptide variant compared to the residual activity after incubation at pH 4.0 of a parent enzyme variant.

The pH stability can be measured as follows. The ZEN-degrading polypeptides are incubated in buffer solutions of different pH values for one hour. Aliquots containing a polypeptide variant are transferred into eight sample tubes containing incubation buffers of eight different pH values. The incubation buffer is Fed State Simulated Gastric Fluid middle Buffer without milk and half-concentrated (Jantratid et al. (2008) 'Dissolution media simulating conditions in the proximal human gastrointestinal tract: an update.' Pharm Res. 2008 July; 25(7):1663-76)). The pH values of the incubation buffer in the eight sample tubes are set to either 3.5, 4.0, 4.2, 4.4, 4.6, 4.8, 5.0, and 6.0. One aliquot of the polypeptide variant is also transferred to one tube containing sample buffer (Teorell Stenhagen buffer, pH 7.5, containing 0.1 mg/ml bovine serum albumin) as positive control. As negative control, 100 µl sample buffer are incubated in 37° C. in a pre-warmed water bath for one hour. After incubation, the samples are tested for their ability to degrade ZEN in assay buffer solution analogously as described elsewhere herein or as described in the examples (e.g. Example 4). The addition of the ZEN degradation assay buffer ensures a constant pH value of pH 7.5 in all of the samples. Samples are taken throughout the ZEN degradation assay reaction and the concentrations of ZEN, hydrolyzed zearalenone (HZEN) and decarboxylated hydrolyzed zearalenone (DHZEN) are analyzed using HPLC-DAD measurement as described e.g. in Example 4. The activities are calculated e.g. as described in Example 4.

An increase in pH stability is defined as an increase of the residual activity of a polypeptide solution after incubation at pH 4.0 compared to the residual activity of a non-mutated parent enzyme solution after the same treatment. The residual activity is defined by the comparison of the activity of the pH-treated polypeptide solution to the activity of the same polypeptide variant solution after incubation at pH 7.5. The residual activity is calculated as follows: Enzymatic activity of the pH-treated sample divided by the enzymatic activity of a control incubated at pH 7.5, multiplied by 100. The following example serves for illustration: If the enzymatic activity of the polypeptide sample after incubation at pH 4.0 is 0.5 U/l and the enzymatic activity of the polypeptide after incubation at pH 7.5 is 2.7 U/l the residual activity is 18.5%. If the residual activity of the parental polypeptide of SEQ ID NO: 1 after incubation at pH 4.0 is measured to be 2.5%, the increase in pH stability of the polypeptide variant compared to the parent polypeptide is 7.4-fold.

The present invention also concerns an α/β-hydrolase obtainable by the method described herein.

The present invention also relates to an α/β-hydrolase having a polypeptide sequence comprising a sequence corresponding to positions 145 to 218 of SEQ ID NO: 1 or a sequence having more than 58% sequence identity to a sequence corresponding to positions 145 to 218 of SEQ ID NO: 1, wherein the polypeptide sequence comprises at least one amino acid substitution
    at a position corresponding to position 160 to 205 of SEQ ID NO: 1, or
    at a position corresponding to position 159 to 204 of SEQ ID NO: 2, or
    at a position corresponding to position 160 to 205 of SEQ ID NO: 3, 4 or 5, or at a position corresponding to position 176 to 222 of SEQ ID NO: 6, wherein the α/β-hydrolase has a more negative GRAVY value of at least 0.6% compared to the GRAVY value of an α/β-hydrolase having a polypeptide sequence of SEQ ID NO: 1.

The present invention also relates to an α/β-hydrolase having a polypeptide sequence comprising a sequence corresponding to positions 161 to 235 of SEQ ID NO: 6 or a sequence having more than 58% sequence identity to a sequence corresponding to positions 161 to 235 of SEQ ID NO: 6, wherein the polypeptide sequence comprises at least one amino acid substitution at a position corresponding to position 160 to 205 of SEQ ID NO: 1, or at a position corresponding to position 159 to 204 of SEQ ID NO: 2, or at a position corresponding to position 160 to 205 of SEQ ID NO: 3, 4 or 5, or at a position corresponding to position 176 to 222 of SEQ ID NO: 6, wherein the α/β-hydrolase has a more negative GRAVY value of at least 0.6% compared to the GRAVY value of an α/β-hydrolase having a polypeptide sequence of SEQ ID NO: 6.

It is also contemplated that the α/β-hydrolase has a lower GRAVY value of at least 3.0%, 4.2%, 4.8%, 6.0%, 6.6%, 7.8%, 10.2%, 12.0% or more compared to the GRAVY value of an α/β-hydrolase having a polypeptide sequence of SEQ ID NO: 1.

It is also contemplated that the α/β-hydrolase has a lower GRAVY value of at least 1.0%, 2.0%, 2.5%, 2.6%, 3.0%, 4.0%, 5.0%, 6.0%, 6.8% or more compared to the GRAVY value of an α/β-hydrolase having a polypeptide sequence of SEQ ID NO: 6.

The present invention also concerns an α/β-hydrolase having a polypeptide sequence comprising a sequence corresponding to positions 145 to 218 of SEQ ID NO: 1 or a sequence having more than 58% sequence identity to a sequence corresponding to positions 145 to 218 of SEQ ID NO: 1, wherein the polypeptide sequence comprises at least one amino acid substitution at a position corresponding to position 185 to 191 of SEQ ID NO: 1, or at a position corresponding to position 184 to 190 of SEQ ID NO: 2 or at a position corresponding to a position 185 to 191 of SEQ ID NO: 3, 4 or 5, or at a position corresponding to a position of 201 to 208 of SEQ ID NO: 6, wherein the amino acid substitution is selected from V→A, G→R, G→S, A→P, A→R, A→D, A→H, A→N, A→G, S→D, P→H, M→D, G→E, I→A, I→V, H→N and Q→K and/or wherein the amino acid(s) are substituted with an amino acid selected from P, R, D, H, G or N, preferably the amino acid is selected from R, D, H, G or N, more preferably the amino acid is selected from R or N. Such α/β-hydrolases can have a higher stability than the same α/β-hydrolase not having this substitution(s) or before introducing these substitutions(s). For example, such a α/β-hydrolase can have a higher stability compared to a α/β-hydrolase of SEQ ID NO: 1.

The present invention also concerns an α/β-hydrolase having a polypeptide sequence comprising a sequence corresponding to positions 161 to 235 of SEQ ID NO: 6 or a sequence having more than 58% sequence identity to a sequence corresponding to positions 161 to 235 of SEQ ID NO: 6, wherein the polypeptide sequence comprises at least one amino acid substitution at a position corresponding to position 185 to 191 of SEQ ID NO: 1, or at a position corresponding to position 184 to 190 of SEQ ID NO: 2 or at a position corresponding to a position 185 to 191 of SEQ ID NO: 3, 4 or 5, or at a position corresponding to a position of 201 to 208 of SEQ ID NO: 6, wherein the amino acid substitution is selected from F→Y or V→C. Such a α/β-hydrolase can have a higher stability than the same α/β-hydrolase not having this substitution(s) or before introducing these substitutions(s). For example, such an α/β-hydrolase can have a higher stability compared to a α/β-hydrolase of SEQ ID NO: 6.

It is envisioned that the α/β-hydrolase as described herein comprises the amino acid(s) substitutions G→R and A→N, preferably G185R and A188N;

G→S and A→R, preferably G185S and A188R;

G→R, A→R, A→H, S→D, P→H and M→D, preferably G185R, A186R, A188H, S189D, P190H and M191D;

V→A, G→R, A→N, G→E, I→A, H→N and Q→K, preferably V160A, G185R, A188N, G199E, I200A, H203N and Q205K;

V→A, G→S, A→R, G→E, I→A, H→N and Q→K, preferably V160A, G185S, A188R, G199E, I200A, H203N and Q205K;

V→A, G→E, I→A, H→N and Q→K, preferably V160A, G199E, I200A, H203N and Q205K,

V→A, G→R, A→R, A→H, G→E, I→V, H→N and Q→K, preferably V160A, G185R, A186R, A188H, G199E, I200V, H203N and Q205K, and/or F→Y and V→C, preferably F183Y and V197C.

The present invention also concerns nucleic acid molecules encoding for an α/β-hydrolase as described herein. The nucleic acid may be introduced or inserted into an expression vector. The term "expression vector" refers to a nucleic acid molecule construct that is able to express a gene in vivo or in vitro. In particular, it can encompass DNA constructs suitable for transferring the polypeptide-encoding nucleotide sequence into the host cell so as to be integrated in the genome or freely located in the extrachromosomal space, and to intracellularly express the polypeptide-encoding nucleotide sequence and, optionally, transport the polypeptide out of the cell.

The expression vector as described herein may be expressed in a host cell. The term "host cell" refers to all cells containing either a nucleotide sequence to be expressed, or an expression vector, and which is able to produce an enzyme or a polypeptide according to the invention. In particular, this refers to prokaryotic and/or eukaryotic cells, preferably *Pichia pastoris, Escherichia coli, Bacillus subtilis, Streptomyces, Hansenula, Trichoderma, Lactobacillus, Aspergillus*, plant cells and/or spores of *Bacillus, Trichoderma* or *Aspergillus*. The name *P. pastoris* used herein is synonymous with the name *Komagataella pastoris, P. pastoris* being the older and *K. pastoris* the systematically newer name (Yamada et al. (1995) 'The Phylogenetic Relationships of Methanol-assimilating Yeasts Based on the Partial Sequences of 18S and 26S Ribosomal RNAs: The Proposal of *Komagataella* Gen. November (Saccharomycetaceae)' Bioscience, Biotechnology and Biochemistry, Vol. 59, issue 3, pp. 439-444). Notably, species of *Komagataella pastoris* have been recently reassigned to be *Komagataella phaffii* (Kurtzman (2009) "Biotechnological strains of *Komagataella* (*Pichia*) *pastoris* are *Komagataella phaffii* as determined from multigene sequence analysis." J Ind Microbiol Biotechnol. 36(11):1435-8). *Komagataella phaffii* as used herein can e.g. relate to strains *Komagataella phaffii* CBS 7435, *Komagataella phaffii* GS115 or *Komagataella phaffii* JC308.

The present invention also relates to a use of an α/β-hydrolase described herein for degrading zearalenone (ZEN).

ZEN is a nonsteroidal estrogenic macrocyclic lactone with the following structural formula, synthesized by way of the polyketide metabolic pathway:

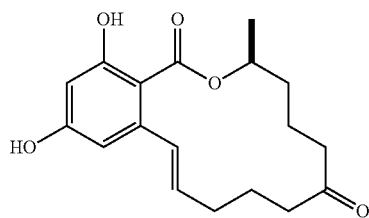

and its name according to the IUPAC nomenclature is (2E,11S)-15,17-dihydroxy-11-methyl-12-oxabicyclo [12.4.0]octadeca-1(18),2,14,16-tetraene-7,13-dione.

However, a variety of ZEN derivatives also occurs in nature and may be formed by enzymatic or chemical modifications of ZEN. Examples include glycosidic ZEN conjugates or those containing sulfate, formed by fungi, plants or a mammalian metabolism as well as ZEN metabolites formed in the human or animal organism, among others. ZEN derivatives are understood below to be ZEN conjugates or ZEN metabolites that occur naturally or are synthesized by chemical or biochemical synthesis but in particular α-zearalenol (α-ZEL; (2E,7R,11S)-7,15,17-trihydroxy-11-methyl-12-oxabicyclo[12.4.0]-octadeca-1(18),2,14,16-tetraen-13-one), β-zearalenol (β-ZEL; (2E,7S,11S)-7,15,17-trihydroxy-11-methyl-12-oxabicyclo[12.4.0]octadeca-1 (18),2,14,16-tetraen-13-one), α-zearalanol (α-ZAL; (7R, 11S)-7,15,17-trihydroxy-11-methyl-12-oxabicyclo[12.4.0] octadeca-1(18),14,16-trien-13-one), β-zearalanol (β-ZAL; (7S,11S)-7,15,17-trihydroxy-11-methyl-12-oxabicyclo [12.4.0]octadeca-1(14),15,17-trien-13-one), zearalenone 14-sulfate (Z14S; [(2E,11S)-15-hydroxy-11-methyl-7,13-dioxo-12-oxabicyclo[12.4.0]octadeca-1(18),2,14,16-tetraen-17-yl] hydrogen sulfate), zearalenone-14-glycoside (Z14G; (2E,11S)-15-hydroxy-11-methyl-17-[(3R,4S,5S,6R)-3,4,5-trihydroxy-6-(hydroxymethyl)-tetrahydropyran-2-yl]oxy-12-oxabicyclo[12.4.0]octadeca 1(18)2,14,16-tetraene-7,13-dione) as well as zearalanone (ZAN; (11S)-15,17-dihydroxy-11-methyl-12-oxabicyclo-[12.4.0]octadeca-1 (18),14,16-triene-7,13-dione).

ZEN as well as ZEN derivatives, in particular α-ZEL, β-ZEL, Z14S, α-ZAL, β-ZAL, Z14G and ZAN can also be detected in processed foods and animal feed products, such as bread or beer because of their high chemical and physical stability.

Hydrolysis of ZEN and ZEN derivatives succeeds with any of the polypeptides of the sequence ID numbers 1 to 6. Hydrolysis of ZEN or its derivatives is believed to occur at the ester group according to the following reaction mechanism:

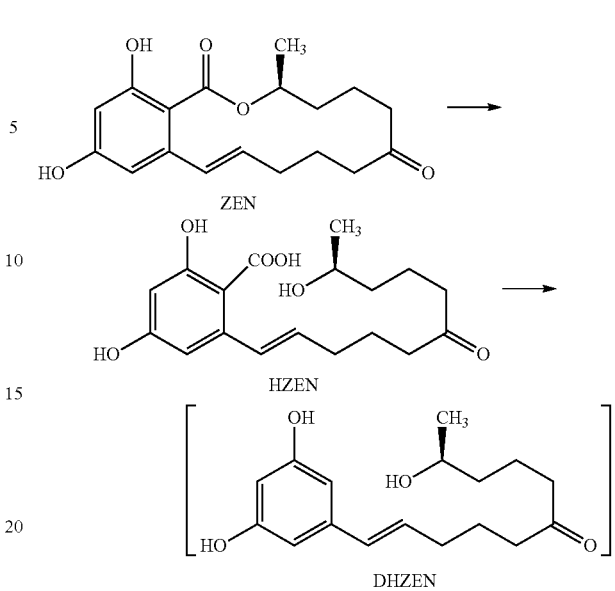

The hydrolysis of ZEN to form nontoxic hydrolyzed zearalenone (HZEN) and/or hydrolyzed ZEN derivatives can take place by the α/β-hydrolases of the present invention. The further decarboxylation of HZEN to decarboxylated hydrolyzed ZEN (DHZEN) and/or decarboxylated hydrolyzed ZEN derivatives is believed to occur spontaneously.

The α/β-hydrolase described herein can be capable of and suitable for degrading ZEN. For example, the α/β-hydrolase, can be suitable for oxygen-independent and cofactor-free hydrolytic cleavage of the ester group of ZEN and/or its derivatives.

ZEN degradation may be measured by adding the α/β-hydrolases of the present invention to Teorell Stenhagen buffer (pH 7.5) with 0.1 mg/ml bovine serum albumin at a temperature of 37° C. The initial substrate concentration in the reaction is 15.71 µM ZEN. ZEN, HZEN, DHZEN and/or other derivates may be detected from samples drawn from the reaction using HPLC or other methods well known to the skilled person.

In particular, ZEN degradation may be measured in sample buffer (Teorell Stenhagen buffer (Stenhagen & Teorell. (1938) Nature 141, 415), pH 7.5, containing 0.1 mg/ml bovine serum albumin at a temperature of 37° C. for 3 hours as follows. The polypeptide/enzyme is diluted with sample buffer and stored on ice until use. As negative control, sample buffer containing 5 µg/ml ZEN is incubated. For the degradation approach, sample buffer containing 5 µg/ml ZEN is mixed with a polypeptide/enzyme solution to achieve a final enzyme concentration which degrades the available ZEN to a degree of 90% to 100% within 3 hours. With the addition of the polypeptide/enzyme to the degradation approach, the reaction is started. No enzyme is added to the negative control. Immediately after each reaction is started, it is vortexed for about 2 seconds and a 0 h sample (100 µl) is transferred into a new reaction tube. The reaction is incubated in a pre-warmed water-bath at 37° C., the sample is heat-inactivated by incubation for 10 minutes at 99° C., centrifuged (2 minutes, 25° C., 14674×g) and 90 µl supernatant is transferred into a HPLC vial with insert. The sample is stored at 4° C. until HPLC-DAD measurement. The sampling is repeated after 0.5, 1.0, 2.0 and 3.0 hours.

ZEN, HZEN and DHZEN concentrations can be analyzed by HPLC-DAD as described in Vekiru et al. (Vekiru et al.

(2016) 'Isolation and characterisation of enzymatic zearalenone hydrolysis reaction products' World Mycotoxin Journal 9:353-363). Analysis is performed on an Agilent 1100 Series HPLC equipped with a diode array detector (DAD) operated at 274 nm. Retention time of the analytes is 7.03 min for ZEN, 5.17 min for HZEN and 5.95 min for DHZEN when separation is done on a Zorbax SB-Aq, 4.6×150 mm, 5 µm column (Agilent Technologies) at 35° C. by using solvent A: 20% methanol in water+5 mM ammonium acetate and solvent B: 90% methanol in water+5 mM ammonium acetate and following gradient: 0-0.1 min 0% phase B, 0.1-3 min linear increase to 90% phase B, 3-5 min linear increase to 100% B which is continued for 1.9 min, then reduced to 0% phase B in 0.1 min. The column is reconditioned for 2.0 min before starting the next run. Flow rate is set at 0.8 ml/min and injection volume to 15 µl.

Quantification is based on calibration with external standards of ZEN, HZEN, and DHZEN. The enzyme activity in Units per liter (U/l) is calculated from the slope of the linear range of ZEN degradation as determined from a plot of the ZEN concentration in a sample vs. the sampling point of time. To determine the amount of enzyme activity in a sample in U/l, the slope of the linear range in a plot as described above can be calculated in µM ZEN per hour and divided by 60 to determine µM/min. By considering possible dilutions and by including these appropriate dilution factors in the calculation, the enzyme activity in a sample can be determined in U/l. The following example serves for illustration: If the slope of the linear range is 10 µM/h the enzyme activity of an undiluted sample is 0.17 U/l; calculated by 10/60=0.17.

In this context it is noted that the term "unit" or "U" refers to the measure of the catalytic activity of an enzyme and is defined as the number of micromoles (µmol) of substrate, i.e. zearalenone in this case, that are reacted or cleaved per minute under defined conditions. By "activity" of an enzyme or polypeptide solution the enzymatic concentration of the enzyme or polypeptide solution is defined, indicated in units per milliliter (U/ml) or in units per liter (U/l) of solution.

The present invention also relates to a composition comprising an α/β-hydrolase as described herein. The composition can be a food or feed additive or a food or feed product.

Methods to prepare such food- and/or feed compositions are known to the skilled person and are inter alia described in WO 99/35240.

The present invention also relates to an α/β-hydrolase or a composition as described herein for use in the treatment or prophylaxis of a disease. The disease can be a disease affecting the hormone balance such as the estrogen balance, especially ZEN caused mycotoxicosis.

The present invention also relates to a kit comprising the α/β-hydrolase or the composition described herein.

The present invention is further characterized by the following items:

1. A method for increasing the stability of an α/β-hydrolase, which α/β-hydrolase comprises a sequence corresponding to positions 145 to 218 of SEQ ID NO: 1, 3, 4, 5 and/or comprises a sequence corresponding to positions 144 to 217 of SEQ ID NO: 2, and/or comprises a sequence corresponding to positions 161 to 235 of SEQ ID NO: 6, and/or a sequence having 58% or more sequence identity to a sequence corresponding to positions 145 to 218 of SEQ ID NO: 1, 3, 4, 5 and/or a sequence having 58% or more sequence identity to a sequence corresponding to positions 144 to 217 of SEQ ID NO: 2 and/or a sequence having 58% or more sequence identity to a sequence corresponding to positions 161 to 235 of SEQ ID NO: 6 (CAP-domain; 58% identity present to the CAP-domain of SEQ ID NO: 1, 2, 3, 4, 5, 6), the method comprising substituting at least one amino acid at a position corresponding to position 160 to 205 of SEQ ID NO: 1, or at a position corresponding to position 159 to 204 of SEQ ID NO: 2, or at a position corresponding to position 160 to 205 of SEQ ID NO: 3, 4, or 5, or at a position corresponding to position 176 to 222 of SEQ ID NO: 6, wherein the amino acid(s) are substituted with an amino acid, which has a more negative hydropathy index than the substituted amino acid,
wherein the hydropathy index is determined by the Kyte and Doolittle hydropathy index, thereby obtaining an α/β-hydrolase with increased stability.

2. The method of item 1, wherein the hydropathy index of a certain amino acid is

| aa | aa | Hydropathy index (Kyte-Doolittle) |
|---|---|---|
| R | Arginine | −4.50 |
| K | Lysine | −3.90 |
| N | Asparagine | −3.50 |
| Q | Glutamine | −3.50 |
| D | Aspartic acid | −3.50 |
| E | Glutamic acid | −3.50 |
| H | Histidine | −3.20 |
| P | Proline | −1.60 |
| Y | Tyrosine | −1.30 |
| W | Tryptophan | −0.90 |
| S | Serine | −0.80 |
| T | Threonine | −0.70 |
| G | Glycine | −0.40 |
| A | Alanine | 1.80 |
| M | Methionine | 1.90 |
| C | Cysteine | 2.50 |
| F | Phenylalanine | 2.80 |
| L | Leucine | 3.80 |
| V | Valine | 4.20 |
| I | Isoleucine | 4.50 |

3. The method of item 1 or 2, wherein the method comprises substituting at least one amino acid at a position corresponding to position 185 to 191 of SEQ ID NO: 1, and/or at a position corresponding to position 184 to 190 of SEQ ID NO: 2 and/or at a position corresponding to position 185 to 191 of SEQ ID NO: 3, 4 or 5 and/or at a position corresponding to position 201 to 208 of SEQ ID NO: 6.

4. The method of any one of the preceding items, wherein the amino acid(s) are substituted with an amino acid selected from R, K, D, Q, D, N, E, P, G, T, S or H.

5. The method of any one of the preceding items, wherein the amino acid(s) are substituted with an amino acid selected from R, K, N, Q, D, E, H, P, Y, W, S, T, G, A, M, C, F, L or V.

6. The method of any one of the preceding items, wherein the amino acid(s) are substituted with an amino acid selected from R, K, N, Q, D, E, H, P, Y, W, S, T or G.

7. The method of any one of the preceding items, wherein the amino acid(s) are substituted with an amino acid selected from R, K, N, Q, D, E, H or P.

8. The method of any one of the preceding items, wherein the amino acid(s) are substituted with an amino acid selected from S, P, R, D, H, G or N.

9. The method of any one of the preceding items, wherein the amino acid(s) are substituted with an amino acid selected from R, D, H, G, N or P.

10. The method of any one of the preceding items, wherein the amino acid(s) are substituted with an amino acid selected from R, D, H, G or N.

11. The method of any one of the preceding items, wherein the amino acid(s) are substituted with an amino acid selected from P, S, R or H.

12. The method of any one of the preceding items, wherein the amino acid(s) are substituted with an amino acid selected from R or N.

13. The method of any one of the preceding items, wherein the amino acid substitution is selected from one or more of V→A, G→R, G→S, A→P, A→R, A→D, A→H, A→N, A→G, S→D, P→H, M→D, G→E, I→A, I→V, H→N and/or Q→K.

14. The method of any one of the preceding items, wherein the amino acid substitution is selected from one or more of V160A, G185R, G185S, A186P, A186R, A188D, A188H, A188N, A188G, A188R, S189D, P190H, M191D, G199E, I200A, I200V, H203N and/or Q205K.

15. The method of any one of the preceding items, wherein the amino acid substitution is selected from one or more of V→A, G→R, G→S, A→P, A→R, A→D, A→H, A→N, A→G, S→D, P→H, M→D, G→E, I→A, I→V, H→N and/or Q→K.

16. The method of any one of the preceding items, wherein amino acid substitution is selected from G185R, A186R, A188R, A188D, A188H, A188N and/or M191D.

17. The method of any one of the preceding items, wherein the increased stability is a decrease in GRAVY value, an increase in pH stability and/or an increase in temperature stability.

18. The method of any one of the preceding items, wherein the GRAVY value is calculated by the sum of the hydropathy values (index) of all amino acids divided by the number of amino acid residues in the sequence (in accordance with calculation of Kyte and Doolittle).

19. The method of any one of the preceding items, wherein the GRAVY value is calculated by dividing the sum of the hydropathy values (index) of all amino acids in a sequence by the total number of amino acids in the sequence.

20. The method of any one of the preceding claims, wherein the amino acid(s) are substituted with an amino acid selected from R, D, H, G, N or P.

21. The method of any one of the preceding items, wherein the method comprises substituting at least one amino acid
 at a position corresponding to position 185 to 191 of SEQ ID NO: 1, and/or
 at a position corresponding to position 184 to 190 of SEQ ID NO: 2 and/or
 at a position corresponding to position 185 to 191 of SEQ ID NO: 3, 4 or 5 and/or
 at a position corresponding to position 201 to 208 of SEQ ID NO: 6, and wherein the amino acid(s) are substituted with an amino acid selected from R, D, H, G, N or P.

22. An α/β-hydrolase obtainable by the method of any one of the preceding items.

23. An α/β-hydrolase, which α/β-hydrolase comprises a sequence corresponding to positions 145 to 218 of SEQ ID NO: 1, 3, 4, 5 and/or comprises a sequence corresponding to positions 144 to 217 of SEQ ID NO: 2, and/or comprises a sequence corresponding to positions 161 to 235 of SEQ ID NO: 6, and/or a sequence having 58% or more sequence identity to a sequence corresponding to positions 145 to 218 of SEQ ID NO: 1, 3, 4, 5 and/or a sequence having 58% or more sequence identity to a sequence corresponding to positions 144 to 217 of SEQ ID NO: 2 and/or a sequence having 58% or more sequence identity to a sequence corresponding to positions 161 to 235 of SEQ ID NO: 6 (CAP-domain; 58% identity present to the CAP-domain of SEQ ID NO: 1, 2, 3, 4, 5, 6),
 wherein the polypeptide sequence comprises at least one amino acid substitution
  at a position corresponding to position 160 to 205 of SEQ ID NO: 1, or
  at a position corresponding to position 159 to 204 of SEQ ID NO: 2, or
  at a position corresponding to position 160 to 205 of SEQ ID NO: 3, 4 or 5, or
  at a position corresponding to position 176 to 222 of SEQ ID NO: 6,
 wherein the α/β-hydrolase has a more negative GRAVY value of at least 0.6% compared to the GRAVY value of an α/β-hydrolase having a polypeptide sequence of SEQ ID NO: 1.

24. An α/β-hydrolase having a polypeptide sequence comprising a sequence corresponding to positions 161 to 235 of SEQ ID NO: 6 or a sequence having more than 58% sequence identity to a sequence corresponding to positions 161 to 235 of SEQ ID NO: 6,
 wherein the polypeptide sequence comprises at least one amino acid substitution
  at a position corresponding to position 160 to 205 of SEQ ID NO: 1, or
  at a position corresponding to position 159 to 204 of SEQ ID NO: 2, or
  at a position corresponding to position 160 to 205 of SEQ ID NO: 3, 4 or 5, or
  at a position corresponding to position 176 to 222 of SEQ ID NO: 6,
 wherein the α/β-hydrolase has a more negative GRAVY value of at least 0.6% compared to the GRAVY value of an α/β-hydrolase having a polypeptide sequence of SEQ ID NO: 6.

25. An α/β-hydrolase having a polypeptide sequence comprising a sequence corresponding to positions 145 to 218 of SEQ ID NO: 1, 3, 4, 5 and/or comprises a sequence corresponding to positions 144 to 217 of SEQ ID NO: 2, and/or comprises a sequence corresponding to positions 161 to 235 of SEQ ID NO: 6, and/or a sequence having 58% or more sequence identity to a sequence corresponding to positions 145 to 218 of SEQ ID NO: 1, 3, 4, 5 and/or a sequence having 58% or more sequence identity to a sequence corresponding to positions 144 to 217 of SEQ ID NO: 2 and/or a sequence having 58% or more sequence identity to a sequence corresponding to positions 161 to 235 of SEQ ID NO: 6 (CAP-domain; 58% identity present to the CAP-domain of SEQ ID NO: 1, 2, 3, 4, 5, 6), comprising
 wherein the polypeptide sequence comprises at least one amino acid substitution
  at a position corresponding to position 185 to 191 of SEQ ID NO: 1, or
  at a position corresponding to position 184 to 190 of SEQ ID NO: 2 or
  at a position corresponding to a position 185 to 191 of SEQ ID NO: 3, 4 or 5, or
  at a position corresponding to a position of 201 to 208 of SEQ ID NO: 6,
   wherein the amino acid substitution is selected from V→A, G→R, G→S, A→P, A→R, A→D, A→H, A→N, A→G, S→D, P→H, M→D, G→E, I→A, I→V, H→N, Q→K, F→Y and/or V→C and/or
wherein the amino acid(s) are substituted with an amino acid selected from P, R, D, H, G or N, preferably the amino acid is selected from R, D, H, G or N, more preferably the amino acid is selected from R or N.

26. The α/β-hydrolase of any one of the preceding items, wherein the α/β-hydrolase comprises the amino acid(s) substitutions
G→R and A-N, preferably G185R and A188N;
G→S and A→R, preferably G185S and A188R;
G→R, A→R, A→H, S→D, P→H and M→D, preferably G185R, A186R, A188H, S189D, P190H and M191D;
V→A, G→R, A→N, G→E, I→A, H→N and Q→K, preferably V160A, G185R, A188N, G199E, I200A, H203N and Q205K;
V→A, G→S, A→R, G→E, I→A, H→N and Q→K, preferably V160A, G185S, A188R, G199E, I200A, H203N and Q205K;
V→A, G→E, I→A, H→N and Q→K, preferably V160A, G199E, I200A, H203N and Q205K;
V→A, G→R, A→R, A→H, G→E, I→A, H→N and Q→K, preferably V160A, G185R, A186R, A188H, G199E, I200A, H203N and Q205K and/or
V→A, G→R, A→R, A→H, G→E, I→V, H→N and Q→K, preferably V160A, G185R, A186R, A188H, G199E, I200V, H203N and Q205K;
V→A, G→R, A→R, A→H, S→D, P→H, M→D, G→E, I→V, H→N and Q→K, preferably V160A, G185R, A186R, A188H, S189D, P190H, M191D, G199E, I200V, H203N and Q205K; and/or
F→Y and V→C, preferably F183Y and V197C.

27. A use of an α/β-hydrolase of any one of the preceding items for degrading zearalenone (ZEN).

28. A composition comprising an α/β-hydrolase of any one of the preceding items, preferably the composition is a food or feed additive or a food or feed product.

29. The α/β-hydrolase or the composition of any one of the preceding items for use in the treatment or prophylaxis of a disease.

30. Kit comprising the α/β-hydrolase or the composition of any one of the preceding items.

31. A method for increasing the stability of an α/β-hydrolase, which α/β-hydrolase comprises a sequence corresponding to positions 160 to 205 of SEQ ID NO: 1, 3, 4, 5 and/or comprises a sequence corresponding to positions 159 to 204 of SEQ ID NO: 2, and/or comprises a sequence corresponding to positions 176 to 222 of SEQ ID NO: 6, and/or a sequence having 58% or more sequence identity to a sequence corresponding to positions 160 to 205 of SEQ ID NO: 1, 3, 4, 5 and/or a sequence having 58% or more sequence identity to a sequence corresponding to positions 159 to 204 of SEQ ID NO: 2 and/or a sequence having 58% or more sequence identity to a sequence corresponding to positions 176 to 222 of SEQ ID NO: 6 (VI-domain; 58% identity present to the VI-domain of SEQ ID NO: 1, 2, 3, 4, 5, 6), comprising
substituting at least one amino acid
at a position corresponding to position 160 to 205 of SEQ ID NO: 1, or
at a position corresponding to position 159 to 204 of SEQ ID NO: 2, or
at a position corresponding to position 160 to 205 of SEQ ID NO: 3, 4, or 5, or
at a position corresponding to position 176 to 222 of SEQ ID NO: 6,
wherein the amino acid(s) are substituted with an amino acid, which has a more negative hydropathy index than the substituted amino acid,
wherein the hydropathy index is determined by the Kyte and Doolittle hydropathy index, thereby obtaining an α/β-hydrolase with increased stability.

32. A method for increasing the stability of an α/β-hydrolase, which α/β-hydrolase comprises a sequence of SEQ ID NO: 1, 2, 3, 4, 5 or 6, the method comprising substituting at least one amino acid
at a position corresponding to position 160 to 205 of SEQ ID NO: 1, or
at a position corresponding to position 159 to 204 of SEQ ID NO: 2, or
at a position corresponding to position 160 to 205 of SEQ ID NO: 3, 4, or 5, or
at a position corresponding to position 176 to 222 of SEQ ID NO: 6,
wherein the amino acid(s) are substituted with an amino acid, which has a more negative hydropathy index than the substituted amino acid,
wherein the hydropathy index is determined by the Kyte and Doolittle hydropathy index, thereby obtaining an α/β-hydrolase with increased stability.

33. An α/β-hydrolase, which α/β-hydrolase comprises a sequence corresponding to positions 160 to 205 of SEQ ID NO: 1, 3, 4, 5 and/or comprises a sequence corresponding to positions 159 to 204 of SEQ ID NO: 2, and/or comprises a sequence corresponding to positions 176 to 222 of SEQ ID NO: 6, and/or a sequence having 58% or more sequence identity to a sequence corresponding to positions 160 to 205 of SEQ ID NO: 1, 3, 4, 5 and/or a sequence having 58% or more sequence identity to a sequence corresponding to positions 159 to 204 of SEQ ID NO: 2 and/or a sequence having 58% or more sequence identity to a sequence corresponding to positions 176 to 222 of SEQ ID NO: 6 (VI-domain; 58% identity present to the VI-domain of SEQ ID NO: 1, 2, 3, 4, 5, 6), wherein the polypeptide sequence comprises at least one amino acid substitution
at a position corresponding to position 160 to 205 of SEQ ID NO: 1, or
at a position corresponding to position 159 to 204 of SEQ ID NO: 2, or
at a position corresponding to position 160 to 205 of SEQ ID NO: 3, 4 or 5, or
at a position corresponding to position 176 to 222 of SEQ ID NO: 6,
wherein the α/β-hydrolase has a more negative GRAVY value of at least 0.6% compared to the GRAVY value of an α/β-hydrolase having a polypeptide sequence of SEQ ID NO: 1.

34. An α/β-hydrolase having a polypeptide sequence comprising a sequence corresponding to positions 145 to 218 of SEQ ID NO: 1, 3, 4, 5 and/or comprises a sequence corresponding to positions 144 to 217 of SEQ ID NO: 2, and/or comprises a sequence corresponding to positions 161 to 235 of SEQ ID NO: 6, and/or a sequence having 58% or more sequence identity to a sequence corresponding to positions 145 to 218 of SEQ ID NO: 1, 3, 4, 5 and/or a sequence having 58% or more sequence identity to a sequence corresponding to positions 144 to 217 of SEQ ID NO: 2 and/or a sequence having 58% or more sequence identity to a sequence corresponding to positions 161 to 235 of SEQ ID NO: 6 (CAP-domain; 58% identity present to the CAP-domain of SEQ ID NO: 1, 2, 3, 4, 5, 6), comprising
wherein the polypeptide sequence comprises at least one amino acid substitution at a position corresponding to position 185 to 191 of SEQ ID NO: 1, or at a position corresponding to position 184 to 190 of SEQ ID NO: 2 or at a position corresponding to a position 185 to 191 of SEQ ID NO: 3, 4 or 5, or at a position corresponding to a position of 201 to 208 of SEQ ID NO: 6, wherein the amino acid substitution is selected from V→A, G→R, G→S, A→P, A→R, A→D, A→H, A→N, A→G, S→D, P→H, M→D, G→E, I→A, I→V, H→N and Q→K and/or wherein the amino acid(s) are substituted with an amino acid selected from P, R, D, H, G or N, preferably the amino acid is selected from R, D, H, G or N, more preferably the amino acid is selected from R or N.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "more than" does not include the concrete number.

For example, less than 20 means less than the number indicated. Similarly, more than or greater than means more than or greater than the indicated number, e.g. more than 80% means more than or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

The following sequences are used in the present application.

TABLE 2

Sequences used in this application.

| SEQ ID NO | Sequence |
|---|---|
| 1 | MVTSPALRDVHVPHAYPEQQVDLGEITMNYAEAGDPDRPA VLLIPEQTGSWWSYEEAMGLLSEHFHVYAVDLRGQGRSSW TPKRYSLDNFGNDLVRFIALVVKRPVVVAGNSSGGVLAAW LSAYSMPGQLRGVLCEDPPFFASELVPAHGHSVRQGAGPV FELFRTYLGDQWSVGDWEGFCRAAGASASPMARSFVADGI PQHLQEYDPEWARVFYEGTVGLSCPHERMLGQVKTPVLLT HHMRGIDPETGNLLGALSDEQALRARRLMDSAGVTVDYES VPDASHMMQSAPARYVEIFTRWAAALAP |
| 2 | MADPAQRDVYVPHAYPEKQADLGEITMNYAEAGEPDMPAV LLIPEQTGSWWGYEEAMGLLAENFHVYAVDLRGQGRSSWA PKRYSLDNFGNDLVRFIALVVKRPVIVAGNSSGGVLAAWL SAYSMPGQVRGALCEDAPFFASELVTTCGHSIRQAAGPMF ELFRTYLGDQWSVGDWTGYCRAADASSSPMARYFVADEIP QHMREYDPEWARAFWEGTVALHCPHEQLLTQVKTPVLLTH HMRDIDPDTGHLVGALSDEQAARARLLMESAGVKVDYASV PDALHMMHQFDPPRYVEIFTQWAATLAA |
| 3 | MVTSPALRDVHVPHAYPEQQVDLGEITMNYAEAGDPGRPA VLLIPEQTGSWWSYEEAMGLLAEHFHVYAVDLRGQGRSSW TPKRYSLDNFGNDLVRFIALVVRRPVVVAGNSSGGVLAAW LSAYSMPGQIRGVLCEDPPFFASELVPAHGHSVRQGAGPV FELFRTYLGDQWSVGDWEGFRSAADASASPMARSFVADTI PQHLKEYDPEWARAFYEGTVGLNCPHERMLNRVNTPVLLT HHMRGTDPETGNLLGALSDEQAAQVRRLMESAGVKVDYES VPDASHMMQSDPARYAEILTPWTAALAP |
| 4 | MVTSPALRDVHVPHAYPEQQVDLGEITMNYAEAGDPDRPA VLLIPEQTGSWWSYEEAMGLLAEHFHVYAVDLRGQGRSSW TPKRYSLDNFGNDLVRFIALVVKRPVVVAGNSSGGVLAAW LSAYSMPGQLRGVLCEDPPFFASELVPAHGHSVRQGAGPV FELFRTYLGDQWSVSDWEGFCRAAGASASPMARSFVADGI PQHLKEYDPEWARAFHEGTVGLNCPHERMLGRVNTPVLLT HHMRGTDPETGNLLGALSDEQAAQARLLMESAGVRVDYES VPDASHMMQSDPARYAEIFTRWAAALAP |
| 5 | MVTSPALRDVHVPHAYPEQQVDLGEITMNYAEAGDPGRPA VLLIPEQTGSWWSYEEAMGLLAEHFHVYAVDLRGQGRSSW TPKRYSLDNFGNDLVRFMALVVRRPVVVAGNSSGGVLAAW LSAYSMPGQIRGVLCEDPPFFASELVPAHGHSVRQGAGPV FELFRTYLGDQWSVGDWEGFRSAAGASASPMARSFVADTI PQHLKEYDPEWARAFYEGTVGLNCPHERMLNRVNTPVLLT HHMRGTDPETGNLLGALSDEQAAQARRLMESAGVKVDYES VPDASHMMQSDPARYAEILTPWAAALAP |
| 6 | MAEEGTRSEAADAATQARQLPDSRNIFVSHRFPERQVDLG EVVMNFAEAGSPDNPALLLLPEQTGSWWSYEPVMGLLAEN FHVFAVDIRGQGRSTWTPRRYSLDNFGNDLVRFIALVIKR PVVVAGNSSGGLLAAWLSAYAMPGQIRAALCEDAPFFASE LVPAYGHSVLQAAGPAFELYRDFLGDQWSIGDWKGFVEAA KASPAKAMQLFPTPDEAPQNLKEYDPEWGRAFFEGTVALH CPHDRMLSQVKTPILITHHARTIDPETGELLGALSDLQAE HAQDIIRSAGVRVDYQSHPDALHMMHLFDPARYAEILTSW SATLPAND |
| 7 | QXAGP |
| 8 | EYDPE |
| 9 | G(F/Y)XXAA |

TABLE 2-continued

Sequences used in this application.

| SEQ ID NO | Sequence |
|---|---|
| 10 | ARXF |
| 11 | QLFP |

Motifs that can flank a VI-domain as described herein are shown as SEQ ID NO: 7 and 8. Motifs that can flank a CAP-loop as described herein are shown as SEQ ID NO: 9, 10, 11. An "X" in a motif can be any amino acid. The second amino acid of the motif of SEQ ID NO: 9 can be either F or Y, as indicated by "(F/Y)". Both, a VI-domain and a CAP-loop are comprised in a CAP-domain that can be located within the excursion between a β-sheet and an α-helix, e.g. between b6 and aD of the α/β-hydrolase as described by Ollis et al. (1992) 'The alpha/beta hydrolase fold' Protein Eng. 5(3):197-211. The VI-domains and CAP-loops are shown underlined for the SEQ ID NO: 1-6.

A better understanding of the present invention and of its advantages will be had from the following examples, offered for illustrative purposes only. The examples are not intended to limit the scope of the present invention in any way.

EXAMPLES OF THE INVENTION

Example 1: Modification, Cloning and Expression of Polynucleotides Encoding Zearalenone-Cleaving Polypeptides Amino acid substitutions, insertions or deletions were performed by mutations of the nucleotide sequences by means of PCR using the QuikChange site-directed mutagenesis kit (Stratagene) according to the manufacturer's instructions. Alternatively, also complete nucleotide sequences were synthesized (e.g. GeneArt Gene Synthesis by Thermo Fisher Scientific). The nucleotide sequences generated by PCR mutagenesis and those obtained from GeneArt were integrated by standard methods in expression vectors for the expression in E. coli. E. coli BL21(DE3) was transformed with the expression vectors and the nucleotide sequences were expressed in that strain (J. M. Cregg, Pichia Protocols, second Edition, ISBN-10: 1588294293, 2007; J. Sambrook et al. 2012, Molecular Cloning, A Laboratory Manual 4th Edition, Cold Spring Harbor). Any other suitable host cell may also be used for this task. The soluble cell lysate of E. coli was used to determine the catalytic properties of the polypeptide variants.

Example 2: Determination of ZEN-Degrading α/β-Hydrolases, their CAP-Domain, their VI-Domain and CAP-Loop To determine if an amino acid sequence is a ZEN-degrading α/β-hydrolase, the sequence of interest was aligned with the sequence of SEQ ID NO: 1 to determine the sequence identity. Furthermore, a topology prediction and homology modeling was performed for the sequence of interest. The sequence alignment was performed with CLC sequence viewer 7.8.1 with the following parameters: Gap open costs 10.0, gap extension costs: 1.0, end gap cost: As any other, alignment: Very accurate.

The topology prediction and homology modeling was performed with YASARA Structure 16.7.22 (1993-2016 by Elmar Krieger, Bioinformatics 30, 2981-2982) by homology modeling with the following parameters: PSI-BLAST iterations: 3, PSI-BLAST E-value: 0.5, Oligomerization state: 4, Templates: 5, with same sequence: 1, alignment per template: 5, modelling speed: Fast, terminal extension: 10, loop samples: 50, use PSSP: Yes. In the YASARA Homology Modeling Report the topology prediction by PSI-Pred secondary structure prediction algorithm (Jones (1999) 'Protein secondary structure prediction based on position-specific scoring matrices' J. Mol. Biol. 292:195-202) was documented. z-scores for all generated homology models were documented. The generated model with the best z-score was taken for structural analysis and determination of the structural features of α/β-hydrolases and the excursions e.g. as described by Ollis et al. (1992) 'The alpha/beta hydrolase fold' Protein Eng. 5(3):197-211.

For identification of a CAP-domain, a VI-domain and a CAP-loop in the new sequence of interest, the secondary structures of the α/β-hydrolase core domain have to be labeled in accordance with FIG. 2a in Ollis et al. (1992) 'The alpha/beta hydrolase fold' Protein Eng. 5(3):197-211. The CAP-domain, the VI-domain as well as the CAP-loop are located within the excursion between b6 and aD of a ZEN-degrading α/β-hydrolase. A CAP-domain can begin shortly after the C-terminal end of the b6 β-strand of the α/β-hydrolase core domain, and can span until the N-terminal start of the aD α-helix of the α/β-hydrolase core domain. The VI-domain is a part of the CAP-domain and begins from the first amino acid after the QXAGP motif present in the CAP-domain and spans until the last amino acid before the EYDPE motif, whereas the EYDPE motif is not part of the VI-domain. The CAP-loop is a part of the VI-domain and begins from the first amino acid after the G(F/Y)XXAA motif present in the VI-domain and spans until the last amino acid before the ARXF motif (or the QLFP motif for SEQ ID NO: 6), whereas the ARXF motif (or the QLFP motif for SEQ ID NO: 6) is not part of the CAP-loop. For example, the positions of the CAP-domains, VI-domains and of the CAP-loops were determined as described herein for the polypeptides of SEQ ID NO: 1-6 and are shown in FIG. 1.

Example 3: Determination of Grand Average of Hydropathy (GRAVY) Value

The grand average of hydropathy (GRAVY) value of an amino acid sequence of a polypeptide is defined by the sum of hydropathy values (Kyte and Doolittle, 1982, cited herein) of all amino acids divided by the polypeptide length, which corresponds to the total number of amino acids of the polypeptide. The GRAVY values were calculated for the polypeptides and defined parts of the polypeptides using the ProtParam program at https://web.expasy.org/protparam (Gasteiger E. et al.; Protein Identification and Analysis Tools on the ExPASy Server, in John M. Walker (ed): The Proteomics Protocols Handbook, Humana Press, 2005, pp. 571-607). The CAP-domain of SEQ ID NO: 1 is defined by the part from the amino acid positions 145 to 218 (both positions included), the VI-domain of SEQ ID NO: 1 is defined as the amino acid sequence from the amino acid positions 160 to 205 (both positions included) and the CAP-loop of SEQ ID NO: 1 is defined by the part of the amino acid sequence from the amino acid positions 185 to 191 (both included). For the entire polypeptide of SEQ ID NO: 1, the calculated GRAVY value is −0.167, for the CAP-domain of SEQ ID NO: 1 the GRAVY value is −0.284, for the VI-domain of SEQ ID NO: 1 the GRAVY value is −0.043, and for the CAP-loop within the CAP-domain of SEQ ID NO: 1 the GRAVY value is +0.271. The CAP-domain, VI-domain and CAP-loop of SEQ ID NO: 6 are defined by the parts of the amino acid positions from 161-235, 176-222, 201-208, respectively (both positions of the indicated ranges are included). For the entire polypeptide of SEQ ID NO: 6, the calculated GRAVY value is −0.192, for the CAP-domain of SEQ ID NO: 6 the GRAVY value is −0.388, for the VI-domain of SEQ ID NO: 6 the GRAVY value is −0.468, and for the CAP-loop of SEQ ID NO: 6 the GRAVY value is −0.362.

The decrease of the GRAVY value in percent of the entire amino acid sequence of a polypeptide caused by at least one mutation relative to the entire amino acid sequence of the non-mutated/non-substituted polypeptide of SEQ ID NO: 1 or 6 was calculated by the difference between the two GRAVY values divided by the GRAVY value of the non-mutated polypeptide, multiplied by 100. For illustration, the calculation for the SEQ ID NO: 1 variant V160A is shown here: ((−0.174)−(−0.167))/(−0.167)×100=4.2%. The results for further examples are listed in FIGS. 2A and 2E.

The decrease of the GRAVY value in percent of the CAP-domain caused by the mutations within the CAP-domain relative to the sequence of the non-mutated CAP-domain of SEQ ID NO: 1 or 6 was calculated by the difference between the two GRAVY values divided by the GRAVY value of the non-mutated CAP-domain, multiplied by 100. For illustration, the calculation for the SEQ ID NO: 1 variant V160A is shown here: ((−0.316)−(−0.284))/(−0.284)×100=11.3%. The results for further examples are listed in FIGS. 2B and 2F.

The decrease of the GRAVY value in percent of the VI-domain caused by mutations within the VI-domain relative to the sequence of the non-mutated VI-domain of SEQ ID NO: 1 or 6 was calculated by the difference between the two GRAVY values divided by the GRAVY value of the non-mutated VI-domain, multiplied by 100. For illustration, the calculation for the SEQ ID NO: 1 variant G185R is shown here: ((−0.133)−(0.043))/(−0.043)×100=209.3%. The results for further examples are listed in FIGS. 2C and 2G.

The decrease of the GRAVY value in percent of the CAP-loop caused by the mutations within the CAP-loop relative to the sequence of the non-mutated CAP-loop of SEQ ID NO: 1 or 6 was calculated by the difference between the two GRAVY values divided by the GRAVY value of the non-mutated CAP-loop, multiplied by 100. For illustration, the calculation the SEQ ID NO: 1 variant G185R is shown here: ((−0.314)−(+0.271))/(+0.271)×100=−215.9%. The value is negative, because the GRAVY value of the parental CAP loop is positive. To simplify the data representation for further examples for mutations, the percent values are shown as positive values in FIG. 2D.

Example 4: Determination of the Activity of ZEN-Degrading Polypeptides

The corresponding genes encoding ZEN-degrading polypeptides were cloned using standard methods, intracellularly expressed in *Escherichia coli*, and the produced polypeptides were isolated from *E. coli* by methods known to a person skilled in the art, e.g. by lysis using a French Press cell. The determination of the protein concentration was performed by means of standard methods, e.g. the BCA method (Pierce BCA Protein Assay KitProd #23225).

The enzyme activity determinations were performed in sample buffer (Teorell Stenhagen buffer (Stenhagen & Teorell. (1938) Nature 141, 415), pH 7.5, containing 0.1 mg/ml bovine serum albumin at a temperature of 37° C. for 3 hours. The polypeptides were diluted with sample buffer and stored on ice until use. A 1500 ppm (w/v) ZEN stock solution in acetonitrile was diluted 1:10 with sample buffer and stored at 25° C. until further dilution for use in a degradation reaction. The degradation approach and one negative control were prepared in reaction tubes. As negative control, sample buffer containing 5 µg/ml ZEN was incubated. For the degradation reaction, sample buffer was mixed with a polypeptide solution to achieve 5 µg/ml final ZEN concentration and a final enzyme concentration that achieved a 90% to 100% ZEN degradation within 3 hours. With the addition of the polypeptide to the ZEN-containing sample buffer, the reaction was started. No enzyme was added to the negative control. Immediately after each reaction was started, it was vortexed for about 2 seconds and a 0 h sample (100 µl) was taken and transferred into a new reaction tube. The reaction was incubated in a pre-warmed water-bath at 37° C., the sample was heat-inactivated by incubation for 10 minutes at 99° C., centrifuged (2 minutes, 25° C., 14674×g) and 90 µl supernatant was transferred into a HPLC vial with insert. The sample was stored at 4° C. until HPLC-DAD measurement. The sampling was repeated after 0.5, 1.0, 2.0 and 3.0 hours.

ZEN, HZEN and DHZEN concentrations were analyzed by HPLC-DAD as described in Vekiru et al. (Vekiru et al. (2016) 'Isolation and characterisation of enzymatic zearalenone hydrolysis reaction products' World Mycotoxin Journal 9:353-363). Analysis was performed on an Agilent 1100 Series HPLC equipped with a DAD detector operated at 274 nm. Retention times of the analytes were 7.03 min for ZEN, 5.17 min for HZEN and 5.95 min for DHZEN when separation was done on a Zorbax SB-Aq, 4.6×150 mm, 5 µm column (Agilent Technologies) at 35° C. by using solvent A: 20% methanol in water+5 mM ammonium acetate and solvent B: 90% methanol in water+5 mM ammonium acetate and following gradient: 0-0.1 min 0% phase B, 0.1-3 min linear increase to 90% phase B, 3-5 min linear increase to 100% B which was held for 1.9 min, coming back to 0% phase B in 0.1 min. The column was reconditioned for 2.0 min before starting the next run. Flow rate was set to 0.8 ml/min and injection volume to 15 µl. Quantification was based on calibration with external standards of ZEN, HZEN, and DHZEN. The enzyme activity in Units per liter (U/l) was calculated from the slope of the linear range of ZEN degradation as determined from a plot of the ZEN concentration in a sample vs. the sampling point of time. To determine the amount of enzyme activity in a sample in U/l, the slope of the linear range in a plot as described above could be calculated in µM ZEN per hour and divided by 60 to determine µM/min. By considering possible dilutions and by including these appropriate dilution factors in the calculation, the enzyme activity in a sample can be determined in U/l. The following example serves for illustration: If the slope of linear range was 10 µM/h the enzyme activity of an undiluted sample was 0.17 U/l; calculated by 10/60=0.17.

Example 5: Temperature Stability of ZEN-Degrading Polypeptides

The production and quantification of the ZEN-degrading polypeptides were performed as described in the examples above. For evaluation of the temperature stability, the ZEN-degrading enzymes were incubated in buffer solution at different temperatures before being tested for their ability to degrade ZEN under optimal conditions. Samples were taken throughout the heat-incubation and residual activities were calculated relative to a non-heat-treated control.

For the temperature stability tests, the polypeptides were diluted with sample buffer (Teorell Stenhagen buffer, pH 7.5, containing 0.1 mg/ml bovine serum albumin) to a concentration of 0.001526923 U/mL and kept on ice until further use. Forty 50 µl aliquots of diluted polypeptide solution were transferred into the tubes of four 12-tube strips (e.g. from starlab) whereby the first tube of each strip and the last tube of each strip were not used but were left empty. The strips were sealed with 12-strip caps (e.g. from starlab). As positive controls, four 50 µl aliquots of diluted enzyme solution were transferred into four PCR tubes. All PCR tubes and strips were kept on ice until the temperature incubation step was started. As negative controls, four 50 µl aliquots of sample buffer were transferred into four PCR tubes. These tubes were stored at 25° C.

The four 12-tube strips were incubated in a pre-heated PCR cycler with a gradient function (e.g. Eppendorf Mastercycler gradient) at a chosen temperature+/−10° C. The temperature gradient (+/−10° C. of the chosen temperature) along the thermoblock of the PCR cycler was calculated automatically by the PCR cycler. The PCR tubes containing the positive controls were incubated on ice, those containing the negative controls were incubated at 25° C. After 0, 5, 10 and 20 minutes, one PCR strip and one negative control tube were transferred to be kept on ice until the end of the incubation, i.e. 20 min after start of the incubation.

After all incubation steps were finished and all strips and tubes were on ice, the ZEN degradation assays were started.

The ZEN degradation assay buffer (Teorell Stenhagen buffer, pH 7.5 containing 0.1 mg/ml bovine serum albumin and 5.3 ppm ZEN) was prepared and 660 µl aliquots of assay buffer were transferred into 48 reaction tubes. The tubes were sealed and kept at 25° C. until the start of the ZEN degradation assays. For the degradation assays, 40 µl of each of the 40 temperature-treated samples from the PCR strips, 40 µl of each of the four negative controls and 40 µl of each of the four positive controls were added to the tubes containing the 660 µl assay buffer, hereby achieving a final ZEN concentration of 5 ppm in the assay reaction. Also, a final concentration of the polypeptides was hereby achieved to degrade ZEN efficiently (i.e. 90%-100% ZEN degradation) within three hours.

By adding either temperature-treated samples, positive or negative controls to the assay buffer, the degradation assay was started. The ZEN degradation reaction was incubated in a pre-warmed water bath at 37° C. Immediately after a degradation reaction was started, it was mixed by vortexing for about 2 seconds and a 0 h sample of 100 µl was transferred into a new reaction tube. Additional samples were drawn from the ZEN degradation assay reaction after 0.5, 1.0, 2.0 and 3.0 hours. As soon as a sample was drawn from the degradation reaction, the enzyme in this sample was heat-inactivated by incubation for 10 minutes at 99° C. Subsequently, the tube was centrifuged (2 minutes, 25° C., 14674×g) and 90 µl of the supernatant was transferred into a HPLC vial with insert. These HPLC vials were stored at 4° C. until HPLC-DAD measurement as described in Example 4.

Using the linear decrease in ZEN concentration as determined by HPLC-DAD analysis of the ZEN degradation samples, enzyme activities were calculated, e.g. in Units per liter (U/l) or in Units per milliliter (U/ml). One Unit was defined as the amount of enzymatic activity that degrades one pmol of ZEN in one minute under the conditions described. The residual activities after incubation at different temperatures for 0, 5, 10 and 20 minutes were calculated as follows: Enzymatic activity in a temperature-treated sample divided by the average of the enzymatic activities from the 0 minute-samples, multiplied by 100.

Temperature stability (T(50%)) was defined as the temperature at which the polypeptides have 50% residual activity after 10 minutes of incubation in comparison with the positive control.

The following example serves for illustration: The parental enzyme has an enzymatic activity of 50 U/ml after a 10-minute incubation on ice and an activity of 25 U/ml after a 10-minute incubation at 59.3° C., the T(50%) value is 59.3° C. If an enzyme variant has a T(50%) value of 61.0° C., the relative increase in the temperature stability (T(50%)) compared to the parental enzyme is 2.9%. This results from the difference between the two T(50%) values of 1.7° C., divided by the T(50%) value of the parental enzyme of 59.3° C., multiplied by 100.

Individual mutations as well as the combination of mutations show an increase in temperature stability as shown in FIGS. 3A and 3B.

Example 6: pH Stability of ZEN Toxin-Degrading Polypeptides

The ZEN-degrading polypeptides were incubated in buffer solution with different pH values for one hour before being tested for their ability to degrade ZEN under optimal conditions. Samples were taken regularly and the concentrations of ZEN, HZEN and DHZEN were analyzed using HPLC-DAD measurement.

The pH values used for the experiment were pH 3.5, 4.0, 4.2, 4.4, 4.6, 4.8, 5.0, and 6.0. The tested polypeptide was transferred into eight sample tubes containing incubation buffer of eight different pH. The incubation buffer was Fed State Simulated Gastric Fluid middle Buffer without milk; half concentrated (Jantratid et al. (2008) 'Dissolution media simulating conditions in the proximal human gastrointestinal tract: an update.' Pharm Res. 2008 July; 25(7):1663-76), set to either pH 3.5, 4.0, 4.2, 4.4, 4.6, 4.8, 5.0, and 6.0. One aliquot of the polypeptide variant was also transferred to one tube containing sample buffer (Teorell Stenhagen buffer, pH 7.5, containing 0.1 mg/ml bovine serum albumin) as positive control. The concentration of the tested polypeptide in the incubation solution was 0.001526923 U/ml in a volume of 100 µl. The tubes were vortexed for about 2 seconds and incubated at 37° C. in a pre-warmed water bath for one hour. As negative control, 100 µl sample buffer were incubated at 37° C. in a pre-warmed water bath for one hour. After one hour of incubation, the ZEN degradation assays with a final concentration of the tested polypeptide of 8.72527E-05 U/ml were performed. To start the ZEN degradation reaction, 40 µl of the incubated samples were transferred to 660 µl assay buffer (Teorell Stenhagen buffer, pH 7.5 containing 0.1 mg/ml bovine serum albumin and 5.3 ppm ZEN). The addition of the assay buffer ensured a constant pH value of pH 7.5 in all of the samples. Immediately after each reaction was started, it was vortexed for about 2 seconds and a 0 h sample (100 µl) was taken and transferred into a new reaction tube. The reaction was incubated in a pre-warmed water bath at 37° C., samples drawn from the reaction were heat-inactivated by incubation for 10 minutes at 99° C., centrifuged (2 minutes, 25° C., 14674×g) and 90 µl supernatant was transferred to a HPLC vial with insert. The sample was stored at 4° C. until HPLC-DAD measurement. Samples were drawn from each degradation assay reaction after 0.5, 1.0, 2.0 and 3.0 hours. ZEN, HZEN and DHZEN were analyzed by HPLC-DAD as described in Example 4 and the activities were calculated as described in Example 4.

An increase in pH stability was defined as an increase of the residual activity of a polypeptide solution after incubation at pH 4.0 compared to the residual activity of a non-mutated parent enzyme solution after the same treatment. The residual activity was defined by the comparison of the activity of the pH-treated polypeptide solution to the activity of the same polypeptide variant solution after incubation at pH 7.5. The residual activity was calculated as follows: Enzymatic activity of the pH-treated sample divided by the enzymatic activity of the control incubated at pH 7.5, multiplied by 100. The following example serves for illustration: If the enzymatic activity of a polypeptide sample after incubation at pH 4.0 was 0.5 U/l and the enzymatic activity of the same polypeptide sample after incubation at pH 7.5 was 2.7 U/l, the residual activity of this polypeptide sample would be 18.5%. Further, if the residual activity of a polypeptide variant after incubation at pH 4.0 was measured to be 18.5%, and the residual activity the parental polypeptide with the SEQ ID NO: 1 after incubation at pH 4.0 was measured to be 2.5%, the increase in pH stability of the polypeptide variant compared to the parent polypeptide is 7.4-fold. Data on increased pH stabilities upon introduction of mutations as described herein is shown in FIG. 4.

Example 7: Testing of Polypeptide Variants for Detoxification of ZEN in Pigs

A total of 12 weaning piglets (female; age 38 days-40 days) were chosen and were randomized according to the trial set up using 12 individual cages of 1 piglet each (4 groups with 3 cages/replicates each). Three test groups received ZEN-degrading enzymes and one control group did not receive any ZEN-degrading enzyme. All piglets were of Austrian genotype Ö-HYB-F1 [(Landrace×Large White)× Pietrain]. All cages were equipped with slatted floors, individual cup drinkers and individual feeding troughs. Climate conditions were computer-operated, regulated automatically according to standard recommendations for weaning piglets and recorded daily.

After housing all piglets were fed with a diet containing in percent (w/w): 29.70% barley, 10.00% wheat, 9.98% corn, 0.27% rapeseed oil, 15.30% fullfat soya, 10.94% maize pressure cooked, 5.00% potato protein, 5.13% dextrose, 3.75% palm kernel, cocos fat, 3.75% lactose, 1.35% lignocellulose, 1.23% mono calcium phosphate, 0.93% calcium carbonate, 0.48% sodium chloride, 0.25% magnesium phosphate, 0.42% vitamin/trace element premix, 0.70% L-Lysine, 0.30% L-Threonine, 0.27% DL-Methionine, 0.15% L-Valine, 0.07% L-Tryptophan, and 0.02% sweetener.

During the experimental period the diet of all groups was supplemented with ZEN to a final concentration of 500 µg ZEN/kg diet. For the test groups the parental polypeptide of SEQ ID NO: 1 and two polypeptide variants thereof were used. The polypeptides were tested in the following concentrations: 2.5 U/kg diet, 5 U/kg diet, 10 U/kg diet and 20 U/kg diet. After an adaption phase of 3 days, the application of the polypeptides was started at a concentration of 2.5 U/kg diet for one day followed by a wash-out day without polypeptide and without ZEN in the diet. After the wash-out day, the non-control piglets received the ZEN-containing diet with the same polypeptide at a concentration of 5 U/kg diet followed by a wash-out day and so on. During the trial, the urine was collected over a period of 12 hours and feces samples were taken once a day. The samples were stored at −20° C. until LC-MS/MS measurement.

In order to normalize the excreted volume of urine, the concentration of creatinine in urine samples was measured. For determination of the creatinine content, the urine samples were diluted 1:5000 with water. Urine samples were diluted with water to a final concentration of 2.5 mM creatinine. 100 µl of diluted urine sample was mixed with 20 µl 100 mM PBS buffer containing 528 U of beta-glucuronidase and incubated at 37° C. over night. After overnight incubation, 380 µl of cold methanol was added, centrifuged at 14674×g, supernatants were transferred to HPLC vials and stored at −20° C. until analysis. For analysis of the feces samples, 500 mg freeze-dried feces were extracted three times (90, 30, and 30 minutes) with 5 ml of acetonitrile/ water (50/50, v/v) each. After each extraction step, samples were clarified by centrifugation (10 min, 14674×g). Aliquots of the pooled supernatants were centrifuged and measured by HPLC-MS/MS. Analyses were performed on an Agilent 1290 series UHPLC system coupled to a 6500 QTrap mass spectrometer. Column temperature was set to 30° C. and flow rate to 0.25 ml/min. Mobile phases A and B consisted of water/acetic acid and acetonitrile/acetic acid (both 99.9/ 0.1, v/v), respectively. The gradient started with 5% B for 0.5 min and continued with a linear increase to 36% B until 17.0 min, and a linear increase to 100% B between 17.0 and 22.0 min, followed by 100% B until 24.0 min and a steep decrease to 5% B between 24.0 and 24.1 min. Finally, the column was re-equilibrated at 5% B until 27.0 min. The injection volume was 2 µl for the urine samples and 3 µl for the feces samples. Separation was performed on a Phenomenex Kinetex C18 column (150×2.1 mm, 2.6 µm). Quantification was based on calibration with external standards of ZEN, α-ZEL, HZEN, and DHZEN. α-ZEL is a metabolite of ZEN with higher estrogenicity and is produced in pigs by hepatic biotransformation (Malekinejad et al. (2006) 'Hydroxysteroid dehydrogenases in bovine and porcine granulosa cells convert zearalenone into its hydroxylated metabolites alpha-zearalenol and beta-zearalenol. Vet Res Commun:445-53). Selected reaction monitoring (SRM) parameters are shown in FIG. 5.

Two tested polypeptide variants the polypeptide with the SEQ ID NO: 1, variant A and variant B, have been tested in addition to the polypeptide with the SEQ ID NO: 1.

The variant A comprises the following mutations compared to SEQ ID NO: 1: V160A/G185R/A186R/A188H/ G199E/I200V/H203N/Q205K.

The variant B comprises the following mutations compared to SEQ ID NO: 1: V160A/G185R/A186R/A188H/ S189D/P190H/M191 D/G199E/I200V/H203N/Q205K.

Results from the analyses of urine and feces samples are shown in FIGS. 6 and 7. The change in the combined concentrations of ZEN plus α-ZEL compared to SEQ ID NO: 1 in percent results from the difference between the concentrations of the two groups, divided by the concentration of the group with SEQ ID NO: 1, multiplied by 100. The increase in the concentration of ZEN plus α-ZEL in the course of the feeding trial in the control group, which did not receive a ZEN-degrading polypeptide in its diet, may be caused by the enterohepatic circulation of ZEN and ZEN derivatives in pigs and consequently an accumulation thereof (Biehl et al. (1993) 'Biliary excretion and enterohepatic cycling of zearalenone in immature pigs.' Toxicol Appl Pharmacol. 1993 July; 121(1):152-9).

Example 8: Testing of Various Concentrations of a Polypeptide for Detoxification of ZEN in Broiler For the feeding trial, 90 day-old, mixed sex broiler chicken (Ross 308) were used. The birds were fed two different diets in two phases. During the adaption period, the birds received phase 1 diet (period live day 1-14), during the experimental period the birds received phase 2 diet (period live day 15-28). Composition of the phase 1 diet in percent (w/w): 55.00% corn, 29.00% soya HP, 1.00% sunflower oil, 6.92% fullfat soya, 0.72% soya protein concentrate, 1.88% palm kernel, cocos fat, 1.96% calcium carbonate, 1.89% mono calcium phosphate, 0.35% sodium bi carbonate, 0.23% sodium chloride, 0.13% magnesium phosphate, 0.24% vitamin/trace element premix, 0.34% L-lysine, 0.12% L-threonine, and 0.24% DL-methionine.

Composition of the phase 2 diet in percent (w/w): 62.00% corn, 23.80% soya HP, 2.00% sunflower oil, 5.53% fullfat soya, 0.58% soya protein concentrate, 1.50% palm kernel, cocos fat, 1.56% calcium carbonate, 1.71% mono calcium phosphate, 0.28% sodium bi carbonate, 0.19% sodium chloride, 0.10% magnesium phosphate, 0.19% vitamin/trace element premix, 0.27% L-lysine, 0.10% L-threonine, and 0.20% DL-methionine.

For the adaption period (14 days), birds were distributed randomly in 3 cages. After the adaption period, birds were evenly distributed by average weight basis into 7 cages (groups) with 8 birds each. The trial duration was 14 days. Climate conditions were regulated according to the breeding company's standard recommendations. Feeding was done manually once a day. Feed and water were available ad libitum. The ZEN concentration in the diet was 400 µg ZEN/kg diet. The control group was fed with diet containing 400 µg ZEN per kg of diet, without the addition of any ZEN-degrading enzyme. The polypeptide variant A (SEQ ID NO: 1 comprising the following mutations V160A/G185R/A186R/A188H/G199E/I200V/H203N/Q205K) was tested in the following concentrations: 5 U/kg diet, 10 U/kg diet, 20 U/kg diet, 40 U/kg diet, 80 U/kg diet and 160 U/kg diet. After euthanasia, crop samples were taken from the birds at the beginning and at the end of the trial. Samples were frozen and lyophilized. For analysis of ZEN, HZEN, and DHZEN, 1 g of each sample was weighted in a 50 ml tube and was extracted twice with 15 ml 80% acetonitrile on a rotary shaker at 25° C. for 30 min. Then the tube was centrifuged for 10 min at 2300×g, 25° C., and the supernatants were pooled in a fresh 50 ml tube. 1 ml was again centrifuged for 5 min at 2300×g, 25° C., and supernatant was transferred to a vial for LC-MS/MS measurement. Samples were stored at –20° C. until measurement and were analyzed by LC-MS/MS. Analyses were performed on an Agilent 1290 series UHPLC system coupled to a 6500+QTrap mass spectrometer. Column temperature was set to 30° C. and flow rate to 0.25 ml/min. Mobile phases A and B consisted of water/acetic acid and acetonitrile/acetic acid (both 99.9/0.1, v/v), respectively. The gradient started with 15% B for 0.5 min and continued with a linear increase to 60% B until 13.5 min, and a steep increase to 100% B between 13.5 and 14.0 min, followed by 100% B until 16.9 min and a steep decrease to 15% B between 16.9 and 17.0 min. Finally, the column was re-equilibrated at 15% B until 20.0 min. The injection volume was 2 µl. Separation was performed on a Phenomenex Kinetex C18 column (150×2.1 mm, 2.6 µm). Quantification was based on calibration with external standards of ZEN, HZEN, and DHZEN. Selected reaction monitoring (SRM) parameters are shown in FIG. 8.

The results from the analysis of the crop samples from the end of the trial are listed in FIG. 9. The reduction of the ZEN concentration in percent was calculated as follows: (ZEN concentration of the control group minus ZEN concentration of a sample group) divided by the ZEN concentration of the control group multiplied by 100.

LIST OF REFERENCES

Altschul Nucl. Acids Res. 25 (1977), 3389-3402
Altschul, J. Mol. Evol. 36 (1993), 290-300
Altschul, J. Mol. Biol. 215 (1990), 403-410
Biehl et al. (1993) 'Biliary excretion and enterohepatic cycling of zearalenone in immature pigs.' Toxicol Appl Pharmacol. 1993 July; 121(1):152-9
Brutlag Comp. App. Biosci. 6 (1990), 237-245 Burnley and Gros (2012) 'phenix.ensemble_refinement: a test study of apo and holo BACE1' Computational crystallography newsletter, volume 4, pp. 51-58
Cregg, Pichia Protocols, second Edition, ISBN-10: 1588294293, 2007
PROTEINS—STRUCTURE AND MOLECULAR PROPERTIES, 2nd Ed., T. E. Creighton, W. H. Freeman and Company, New York (1993)
Elmar Krieger, Bioinformatics 30, 2981-2982
Gasteiger E. et al.; Protein Identification and Analysis Tools on the ExPASy Server, in John M. Walker (ed): The Proteomics Protocols Handbook, Humana Press, 2005, pp. 571-607
Henikoff Proc. Natl. Acad. Sci., USA, 89, (1989), 10915
Henikoff and Henikoff (1992) 'Amino acid substitution matrices from protein blocks.' Proc Natl Acad Sci USA. 1992 Nov. 15; 89(22):10915-9
Jantratid et al. (2008) 'Dissolution media simulating conditions in the proximal human gastrointestinal tract: an update.' Pharm Res. 2008 July; 25(7):1663-76
Jones (1999) 'Protein secondary structure prediction based on position-specific scoring matrices' J. Mol. Biol. 292: 195-202
POST-TRANSLATIONAL COVALENT MODIFICATION OF PROTEINS, B. C. Johnson, Ed., Academic Press, New York (1983), pgs. 1-12; Seifter, Meth. Enzymol. 182 (1990), 626-646
Kourist et al. (2010) 'The alpha/beta-hydrolase fold 3DM database (ABHDB) as a tool for protein engineering.' Chembiochem. 11(12):1635-43
Kurtzman (2009) "Biotechnological strains of Komagataella (Pichia) pastoris are Komagataella phaffii as determined from multigene sequence analysis." J Ind Microbiol Biotechnol. 36(11):1435-8
Kyte and Doolittle (1983) "A simple method for displaying the hydropathic character of a protein". J. Mol. Biol. 157 (1): 105-32
Lenfant et al. (2013) 'ESTHER, the database of the α/β-hydrolase fold superfamily of proteins: tools to explore diversity of functions' Nucleic Acids Research, Volume 41, Issue D1, D423-D429
Malekinejad et al. (2006) 'Hydroxysteroid dehydrogenases in bovine and porcine granulosa cells convert zearalenone into its hydroxylated metabolites alpha-zearalenol and beta-zearalenol. Vet Res Commun:445-53
Mindrebo et al. (2016) 'Unveiling the functional diversity of the Alpha-Beta hydrolase fold in plants' Curr Opin Struct Biol. 233-246
Ollis et al. (1992) 'The alpha/beta hydrolase fold' Protein Eng. 5(3):197-211
Rattan, Ann. NY Acad. Sci. 663 (1992); 48-62
Schatzmayr and Streit (2013) 'Global occurrence of mycotoxins in the food and feed chain: Facts and figures.' World Mycotoxin Journal 6(3):213-222

Sambrook et al. 2012, Molecular Cloning, A Laboratory Manual 4th Edition, Cold Spring Harbor
Stenhagen & Teorell. (1938) Nature 141, 415
Thompson Nucl. Acids Res. 2 (1994), 4673-4680
Vekiru et al. (2016) 'Isolation and characterisation of enzymatic zearalenone hydrolysis reaction products' World Mycotoxin Journal 9:353-363)

Yamada et al. (1995) 'The Phylogenetic Relationships of Methanol-assimilating Yeasts Based on the Partial Sequences of 18S and 26S Ribosomal RNAs: The Proposal of *Komagataella* Gen. November (Saccharomycetaceae)' Bioscience, Biotechnology and Biochemistry, Vol. 59, issue 3, pp. 439-444).

The invention claimed is:

1. A method for increasing the stability of an α/β-hydrolase, which α/β-hydrolase comprises a sequence corresponding to positions 145 to 218 of SEQ ID NO: 1 or a sequence having 80% or more sequence identity to a sequence corresponding to positions 145 to 218 of SEQ ID NO: 1, comprising
    substituting at least one amino acid
        at a position corresponding to position 160 to 205 of SEQ ID NO: 1, or
        at a position corresponding to position 159 to 204 of SEQ ID NO: 2, or
        at a position corresponding to position 160 to 205 of SEQ ID NO: 3, 4, or 5, or
        at a position corresponding to position 176 to 222 of SEQ ID NO: 6,
    wherein the amino acid(s) are substituted with an amino acid which has a more negative hydropathy index than the substituted amino acid,
    wherein the hydropathy index is determined by the Kyte and Doolittle hydropathy index, thereby obtaining an α/β-hydrolase with increased stability compared to the α/β-hydrolase before substituting said amino acid(s).

2. The method of claim 1, wherein the method comprises substituting at least one amino acid
    at a position corresponding to position 185 to 191 of SEQ ID NO: 1, and/or
    at a position corresponding to position 184 to 190 of SEQ ID NO: 2 and/or
    at a position corresponding to position 185 to 191 of SEQ ID NO: 3, 4 or 5 and/or
    at a position corresponding to position 201 to 208 of SEQ ID NO: 6.

3. The method of claim 1, wherein the amino acid(s) are substituted with an amino acid selected from R, K, N, Q, D, E, H, P, Y, W, S, T, G, A, M, C, F, L, or V.

4. The method of claim 3, wherein the amino acid(s) are substituted with an amino acid selected from R, K, N, Q, D, E, H, P, Y, W, S, T, or G.

5. The method of claim 4, wherein the amino acid(s) are substituted with an amino acid selected from R, K, N, Q, D, E, H, or P.

6. The method of claim 1, wherein the amino acid(s) are substituted with an amino acid selected from R, D, H, G, N, or P.

7. The method of claim 6, wherein the amino acid(s) are substituted with an amino acid selected from R, D, H, G, or N.

8. The method of claim 7, wherein the amino acid(s) are substituted with an amino acid selected from R or N.

9. The method of claim 1, wherein the amino acid(s) are substituted with an amino acid to provide an amino acid substitution that is selected from one or more of V160A, G185R, G185S, A186P, A186R, A188D, A188H, A188N, A188G, A188R, S189D, P190H, M191D, G199E, I200A, I200V, H203N, and/or Q205K.

10. The method of claim 9, wherein the amino acid substitution is selected from G185R, A186R, A188R, A188D, A188H, A188N, and/or M191D.

11. The method of claim 1, wherein the increased stability is a decrease in grand average of hydropathy (GRAVY) value, an increase in pH stability and/or an increase in temperature stability.

* * * * *